United States Patent
Xie et al.

(10) Patent No.: US 9,631,044 B2
(45) Date of Patent: Apr. 25, 2017

(54) COMB-LIKE POLYURETHANE AND METHODS FOR PREPARING AND USING THE SAME

(71) Applicants: SICHUAN UNIVERSITY, Chengdu (CN); LAVAL UNIVERSITY, Quebec (CA)

(72) Inventors: Xingyi Xie, Chengdu (CN); Ze Zhang, Quebec (CA); Xiangyang Wu, Chengdu (CN); Qiang Fu, Chengdu (CN); Yinping Zhong, Chengdu (CN)

(73) Assignees: SICHUAN UNIVERSITY, Chengdu (CN); LAVAL UNIVERSITY, Quebec (CA)

( * ) Notice: Subject to any disclaimer, the term of this patent is extended or adjusted under 35 U.S.C. 154(b) by 0 days.

(21) Appl. No.: 14/880,306

(22) Filed: Oct. 12, 2015

(65) Prior Publication Data
US 2016/0102167 A1  Apr. 14, 2016

Related U.S. Application Data

(63) Continuation-in-part of application No. PCT/CN2014/000067, filed on Jan. 20, 2014.

(30) Foreign Application Priority Data

Apr. 10, 2013 (CN) .......................... 2013 1 0123610

(51) Int. Cl.
| | | |
|---|---|---|
| *C08G 18/72* | (2006.01) | |
| *C08G 18/48* | (2006.01) | |
| *C08G 18/28* | (2006.01) | |
| *C08G 18/34* | (2006.01) | |
| *C08G 18/10* | (2006.01) | |
| *C12N 5/071* | (2010.01) | |

(52) U.S. Cl.
CPC ............ *C08G 18/72* (2013.01); *C08G 18/10* (2013.01); *C08G 18/28* (2013.01); *C08G 18/34* (2013.01); *C08G 18/48* (2013.01); *C12N 5/0691* (2013.01); *C12N 2501/165* (2013.01); *C12N 2533/30* (2013.01)

(58) Field of Classification Search
CPC ........ C08G 18/72; C08G 18/48; C08G 18/28; C08G 18/34; C08G 18/10; C12N 5/0691; C12N 2501/165; C12N 2533/30
See application file for complete search history.

(56) References Cited

U.S. PATENT DOCUMENTS 4,496,708 A  1/1985  Dehm et al.

FOREIGN PATENT DOCUMENTS

| CN | 103224607 A | 7/2013 |
|---|---|---|
| DE | 3109700 A1 | 9/1982 |
| EP | 2431398 A1 | 3/2012 |

OTHER PUBLICATIONS

J. M. Orban et al, Easily grafted polyurethanes with reactive main chain functional groups. Synthesis, characterization, and antithrombogenicity of poly(ethylene glycol)-grafted poly(urethanes), Journal of Polymer Science: Part A: Polymer Chemistry, 1999, pp. 3441-3448, vol. 37, John Wiley & Sons, Inc., United States.

D. K. Han et al, Heparin-like anticoagulant activity of sulphonated poly(ethylene oxide) and sulphonated poly (ethylene oxide)-grafted polyurethane, Biomaterials, 1995, pp. 467-471, vol. 16, issue 6, Elsevier, Netherlands.

*Primary Examiner* — Rabon Sergent
(74) *Attorney, Agent, or Firm* — Matthias Scholl, PC; Matthias Scholl

(57) ABSTRACT

A method for preparing a comb-like polyurethane, including: 1) adding a diol to a reaction vessel, stirring, heating, vacuum dehydrating, and cooling the diol; adding a diisocyanate to the diol, and pre-polymerizing the diisocyanate and the diol under vacuum to yield a polyurethane prepolymer; 2) dissolving lysine in a mixture of water and an organic solvent to yield a first solution, adding the first solution to the polyurethane prepolymer to yield a first reaction mixture; stopping stirring and allowing the first reaction mixture to stand for between 10 and 12 hrs, pouring the first reaction mixture into water, and drying a precipitate to yield a polyurethane elastomer containing carboxyl groups; 3) dissolving the polyurethane elastomer in an organic solvent to yield a second solution; adding an epoxy-terminated polyethylene glycol to the second solution, and stirring a resulting mixture at between 110 and 130° C.

5 Claims, 15 Drawing Sheets

FIG. 14

Examples to Synthesize Polyurethane elastomer containing carboxyl groups

| Examples | Macromolecular Diols | | | Diisocyanate | | Lysine | Content of the Water(g) | First Solvent | | Molar Ratio | Hard Segment Content | Solid Content |
|---|---|---|---|---|---|---|---|---|---|---|---|---|
| | Types | Number Average Molecular Weight | Content(g) | Types | Content(g) | Content(g) | | Organic Solvent Types | Content(g) | | | |
| 1 | PCD | 500 | 20 | HDI | 10.63 | 2.92 | 16.82 | THF | 66.36 | 1:1.58:0.50 | 40.39% | 40.33% |
| 2 | PCD | 860 | 8.6 | MDI | 5.51 | 1.46 | 10.11 | THF | 32.2 | 1:2.2:1 | 44.77% | 36.80% |
| 3 | PCD | 1000 | 10 | MDI | 5.51 | 1.46 | 7.16 | THF | 35.31 | 1:2.2:1 | 41.07% | 39.96% |
| 4 | PCD | 1500 | 30 | TDI | 11.08 | 5.85 | 20.35 | DMF | 113.55 | 1:3.18:2 | 36.08% | 35.05% |
| 5 | PCD | 2000 | 20 | IPDI | 6.87 | 2.92 | 13.28 | DMSO | 65.55 | 1:3.09:2 | 32.86% | 37.79% |
| 6 | PCD | 3000 | 30 | HDI | 11.61 | 8.33 | 14.65 | DMAc | 110.55 | 1:6.9:5.7 | 39.93% | 39.89% |
| 7 | PCD | 4000 | 40 | LDI | 16 | 8.77 | 33.85 | THF | 129.55 | 1:7.08:6 | 38.24% | 39.64% |
| 8 | PTMG | 500 | 10 | MDI | 7.81 | 1.46 | 9.45 | DMSO | 38.55 | 1:1.56:0.5 | 48.11% | 40.15% |
| 9 | PTMG | 1000 | 20 | TDI | 8.36 | 2.92 | 13.25 | DMAc | 75.25 | 1:2.4:1 | 36.06% | 35.34% |
| 10 | PTMG | 1500 | 15 | IPDI | 6.62 | 2.19 | 19.98 | DMF | 50.34 | 1:2.98:1.5 | 37.00% | 33.86% |
| 11 | PTMG | 2000 | 20 | HDI | 5.95 | 2.92 | 9.85 | DMSO | 64.65 | 1:3.54:2 | 30.72% | 38.75% |
| 12 | PTMG | 3000 | 15 | TDI | 4.18 | 2.63 | 7.21 | THF | 48.59 | 1:4.8:3.6 | 31.22% | 39.09% |
| 13 | PCL | 500 | 10 | LDI | 7 | 1.46 | 8.55 | DMF | 40.15 | 1:1.55:0.5 | 45.83% | 37.91% |
| 14 | PCL | 1000 | 20 | MDI | 11.11 | 2.92 | 8.73 | DMAc | 74.57 | 1:2.22:1 | 41.23% | 40.85% |
| 15 | PCL | 1500 | 30 | LDI | 10.67 | 2.92 | 13.66 | DMSO | 92.84 | 1:2.36:1 | 31.18% | 40.93% |
| 16 | PCL | 2000 | 20 | TDI | 6.22 | 3.36 | 11.14 | DMF | 60.26 | 1:3.57:2.3 | 32.39% | 41.43% |
| 17 | PCL | 3000 | 15 | LDI | 5.29 | 2.49 | 9.69 | THF | 50.11 | 1:4.68:3.4 | 34.15% | 38.09% |
| 18 | PCL | 4000 | 20 | HDI | 6.05 | 4.39 | 9.89 | DMSO | 66.61 | 1:7.2:6 | 34.30% | 39.79% |
| 19 | PPG | 500 | 10 | TDI | 5.64 | 1.46 | 6.85 | DMAc | 49.65 | 1:1.62:0.5 | 41.52% | 30.27% |
| 20 | PPG | 1000 | 20 | MDI | 11.51 | 2.92 | 12.78 | DMSO | 72.69 | 1:2.3:1 | 41.91% | 40.28% |
| 21 | PPG | 1500 | 30 | HDI | 9.92 | 4.39 | 14.22 | DMF | 97.85 | 1:2.95:1.5 | 32.30% | 39.54% |
| 22 | PPG | 2000 | 20 | IPDI | 5.16 | 1.46 | 12.92 | DMF | 60.62 | 1:2.32:1 | 24.87% | 36.20% |
| 23 | PPG | 3000 | 15 | LDI | 5.33 | 2.63 | 17.92 | THF | 42.88 | 1:4.72:3.6 | 34.67% | 37.76% |
| 24 | PPG | 4000 | 20 | TDI | 5.05 | 3.44 | 9.88 | DMF | 63.36 | 1:5.8:4.7 | 29.80% | 38.90% |
| 25 | HAPHD | 500 | 10 | LDI | 8.63 | 2.19 | 8.76 | DMAc | 45.16 | 1:1.91:0.75 | 51.97% | 38.61% |
| 26 | HAPHD | 1000 | 20 | HDI | 6.89 | 2.19 | 9.42 | DMSO | 65.34 | 1:2.05:0.75 | 31.22% | 38.90% |
| 27 | HAPHD | 1500 | 30 | IPDI | 10.49 | 2.92 | 11.87 | DMF | 100.28 | 1:2.36:1 | 30.89% | 38.71% |
| 28 | HAPHD | 2000 | 20 | MDI | 8.71 | 2.92 | 11.96 | THF | 69.69 | 1:3.48:2 | 36.77% | 38.74% |
| 29 | HAPHD | 3000 | 15 | TDI | 4.11 | 2.63 | 6.88 | DMSO | 46.89 | 1:4.72:3.6 | 31.00% | 40.43% |
| 30 | HAPHD | 4000 | 20 | HDI | 5 | 3.44 | 9.52 | DMF | 68.18 | 1:5.95:4.7 | 29.68% | 36.60% |

| Examples | Method for Synthesizing Polyurethane elastomer containing carboxyl groups | | | | | Carboxyl Equivalent of the Product (mmol/g) |
|---|---|---|---|---|---|---|
| | Dehydrating macromolecular diol | | Prepolymerization Reaction | | Chain Extending Reaction | |
| | Temperature (°C) | Time (min) | Temperature (°C) | Time (min) | Time (min) | |
| 1 | 110 | 180 | 70 | 3 | 20 | 0.6 |
| 2 | 100 | 90 | 50 | 3 | 20 | 0.642 |
| 3 | 100 | 120 | 55 | 2 | 10 | 0.589 |
| 4 | 120 | 180 | 60 | 3.5 | 30 | 0.852 |
| 5 | 110 | 240 | 60 | 3 | 20 | 0.671 |
| 6 | 120 | 180 | 60 | 3.5 | 30 | 1.141 |
| 7 | 120 | 240 | 80 | 4 | 30 | 0.926 |
| 8 | 100 | 150 | 60 | 2 | 15 | 0.518 |
| 9 | 110 | 180 | 70 | 3 | 20 | 0.639 |
| 10 | 100 | 240 | 55 | 3 | 15 | 0.63 |
| 11 | 110 | 240 | 60 | 3 | 15 | 0.693 |
| 12 | 110 | 180 | 60 | 3 | 15 | 0.825 |
| 13 | 100 | 120 | 55 | 3 | 10 | 0.542 |
| 14 | 110 | 180 | 70 | 4 | 20 | 0.588 |
| 15 | 120 | 180 | 70 | 4 | 25 | 0.459 |
| 16 | 110 | 180 | 60 | 3 | 20 | 0.778 |
| 17 | 110 | 150 | 80 | 1 | 15 | 0.746 |
| 18 | 110 | 180 | 60 | 3 | 20 | 0.985 |
| 19 | 100 | 120 | 60 | 2.5 | 10 | 0.585 |
| 20 | 110 | 180 | 60 | 3.5 | 20 | 0.343 |
| 21 | 120 | 240 | 60 | 3 | 25 | 0.677 |
| 22 | 110 | 180 | 60 | 3.5 | 20 | 0.632 |
| 23 | 110 | 120 | 55 | 3 | 15 | 0.784 |
| 24 | 110 | 180 | 70 | 2 | 15 | 0.828 |
| 25 | 120 | 90 | 60 | 2 | 15 | 0.721 |
| 26 | 110 | 180 | 60 | 3 | 20 | 0.516 |
| 27 | 120 | 180 | 70 | 4 | 25 | 0.461 |
| 28 | 110 | 240 | 60 | 3.5 | 20 | 0.623 |
| 29 | 110 | 120 | 55 | 3 | 15 | 0.828 |
| 30 | 110 | 180 | 60 | 3 | 15 | 0.828 |

FIG. 15

| Examples | Polyurethane elastomer containing carboxyl groups | | | PEG | | | | Second Solvent | | Parameters of the Method | |
|---|---|---|---|---|---|---|---|---|---|---|---|
| | Sources | Content (g) | Molar Weight of Carboxyl (mmol) | Types | Number Average Molecular Weight | Content(g) | Molar weight (mmol) | Types | Content (g) | Temperature (°C) | Time (h) |
| 31 | Example 2 | 0.78 | 0.5 | PN | 200 | 0.1 | 0.5 | DMF | 39 | Room Temperature | 20 |
| 32 | Example 8 | 1.54 | 0.8 | PN | 800 | 0.64 | 0.8 | DMSO | 22 | Room Temperature | 30 |
| 33 | Example 11 | 1.44 | 1 | PN | 1600 | 1.6 | 1 | DMAc | 36 | Room Temperature | 25 |
| 34 | Example 16 | 1.54 | 1.2 | PN | 4000 | 4.8 | 1.2 | DMF | 17.11 | Room Temperature | 26 |
| 35 | Example 6 | 1.23 | 1.4 | PN | 5000 | 7 | 1.4 | DMAc | 20.5 | Room Temperature | 22 |
| 36 | Example 19 | 2.74 | 1.6 | PN | 6000 | 9.6 | 1.6 | DMF | 27.4 | Room Temperature | 28 |
| 37 | Example 24 | 2.42 | 2 | PN | 8000 | 16 | 2 | DMSO | 30.25 | Room Temperature | 24 |
| 38 | Example 16 | 1.29 | 1 | PO | 200 | 0.2 | 1 | DMF | 64.5 | 112 | 22 |
| 39 | Example 2 | 2.8 | 1.8 | PO | 526 | 0.95 | 1.8 | DMF | 40 | 110 | 30 |
| 40 | Example 9 | 3.13 | 2 | PO | 1000 | 2 | 2 | DMSO | 78.25 | 123 | 28 |
| 41 | Example 14 | 3.4 | 2 | PO | 2200 | 4.4 | 2 | DMSO | 37.78 | 118 | 25 |
| 42 | Example 22 | 3.8 | 1.43 | PO | 3000 | 4.29 | 1.43 | DMAc | 63.33 | 120 | 27 |
| 43 | Example 29 | 3.38 | 2.8 | PO | 4500 | 12.6 | 2.8 | DMSO | 33.8 | 115 | 24 |
| 44 | Example 28 | 5.14 | 3.25 | PO | 6500 | 21.13 | 3.25 | DMF | 64.25 | 127 | 29 |
| 45 | Example 10 | 5.71 | 3.6 | PO | 7000 | 25.2 | 3.6 | DMAc | 95.17 | 130 | 20 |
| 46 | Example 18 | 4.06 | 4 | PO | 8000 | 32 | 4 | THF | 50.75 | 125 | 26 |

FIG. 16

| Example | Reaction for Synthesizing Diamine Chain Extender with PEG side chain ||||||| BOC Removal || Number Average Molecular Weight of the Synthesized Diamine Chain Extender |
| | DiBoc-Lysine-NH-PEG Synthesis |||||| | | | |
| | DiBoc-Lysine-NH₂ Content (g) | DCC Content (g) | NHS Content (g) | PEG |||  Dichloromethane Content (g) | Trifluoroacetic Acid Content (g) | |
| | | | | Polymerization Degree (n) | Number Average Molecular Weight | Content (g) | | | |
| 48 | 5.82 | 7.43 | 3.45 | 4 | 310 | 9.3 | 45.24 | 12.28 | 614 |
| 49 | 5.44 | 6.93 | 3.22 | 7 | 442 | 12.38 | 48.24 | 12.28 | 746 |
| 50 | 6.21 | 7.92 | 3.68 | 13 | 706 | 22.59 | 55.24 | 12.28 | 1010 |
| 51 | 5.44 | 6.93 | 3.22 | 24 | 1190 | 33.32 | 65.24 | 12.28 | 1494 |
| 52 | 4.66 | 5.94 | 2.76 | 36 | 1718 | 41.23 | 88.24 | 12.28 | 2022 |
| 53 | 3.11 | 3.96 | 1.84 | 59 | 2730 | 43.68 | 108.1 | 11.14 | 3034 |
| 54 | 2.72 | 3.47 | 1.61 | 73 | 3346 | 46.84 | 116.12 | 11.14 | 3650 |
| 55 | 1.94 | 2.48 | 1.15 | 81 | 3698 | 36.98 | 75.12 | 11.14 | 4002 |
| 56 | 1.55 | 1.98 | 0.92 | 100 | 4534 | 36.27 | 72.44 | 8.68 | 4838 |
| 57 | 1.55 | 1.98 | 0.92 | 110 | 4974 | 39.79 | 82.44 | 8.68 | 5278 |
| 58 | 1.16 | 1.49 | 0.69 | 127 | 5722 | 34.33 | 68.44 | 8.68 | 6026 |
| 59 | 1.16 | 1.49 | 0.69 | 136 | 6118 | 36.71 | 74.44 | 8.68 | 6422 |
| 60 | 1.16 | 1.49 | 0.69 | 149 | 6690 | 40.14 | 84.68 | 5.46 | 6994 |
| 61 | 0.78 | 0.99 | 0.46 | 163 | 7306 | 29.22 | 62.68 | 5.46 | 7610 |
| 62 | 0.78 | 0.99 | 0.46 | 172 | 7702 | 30.81 | 63.68 | 5.46 | 8006 |
| 63 | 0.78 | 0.99 | 0.46 | 180 | 8054 | 32.22 | 69.68 | 5.46 | 8358 |

| Examples | Macromolecular Diols | | | Reaction for Synthesizing Polyurethane with Carboxyl-Terminated PEG Side Chain | | | | | | | | | | |
|---|---|---|---|---|---|---|---|---|---|---|---|---|---|---|
| | | | | Diisocyanate | | Lysine | | Chain Extender Lysine-NH-PEG solution | | | | Molar Ratio | Hard Segment Content | Solid Content |
| | Types | Number Average Molecular Weight | Content(g) | Types | Content(g) | Content(g) | Content of water(g) | Sources | Polymerization degree (n) | Content(g) | THF or Second Solvent | | | |
| | | | | | | | | | | | Types | Content(g) | | |
| 64 | PTMG | 1500 | 15 | IPDI | 6.62 | 1.97 | 19.84 | Example 48 | 4 | 0.92 | DMF | 90.18 | 1: 2.98: 1.35: 0.15 | 37.02% | 17.80% |
| 65 | PCD | 1000 | 10 | MDI | 5.51 | 1.24 | 15.16 | Example 49 | 7 | 1.12 | THF | 63.17 | 1: 2.2: 0.85: 0.15 | 41.06% | 17.80% |
| 66 | PPG | 1000 | 10 | MDI | 5.76 | 1.17 | 16.18 | Example 50 | 13 | 2.02 | THF | 62.22 | 1: 2.3: 0.8: 0.2 | 41.92% | 18.01% |
| 67 | PTMG | 500 | 2.5 | TDI | 1.92 | 0.37 | 8.31 | Example 51 | 24 | 3.74 | DMAc | 27.71 | 1: 2.2: 0.5: 0.5 | 51.43% | 12.50% |
| 68 | PCL | 1500 | 15 | LDI | 7.59 | 1.61 | 16.44 | Example 52 | 36 | 18.2 | DMSO | 126.45 | 1: 3.36: 1.1: 0.9 | 41.22% | 15.15% |
| 69 | HAPHD | 1500 | 7.5 | IPDI | 4.97 | 1.64 | 15.14 | Example 53 | 59 | 14.56 | DMF | 75.69 | 1: 4.47: 2.24: 0.96 | 49.35% | 14.02% |
| 70 | PCD | 4000 | 20 | HDI | 5.95 | 2.85 | 16.31 | Example 55 | 81 | 42.02 | THF | 135.95 | 1: 7.08: 3.9: 2.1 | 34.08% | 16.62% |
| 71 | PTMG | 3000 | 15 | TDI | 4.18 | 1.58 | 18.02 | Example 58 | 127 | 43.39 | THF | 150.16 | 1: 4.8: 2.16: 1.44 | 31.23% | 11.48% |
| 72 | PPG | 2000 | 20 | IPDI | 11.83 | 4.39 | 21.37 | Example 60 | 149 | 69.94 | DMSO | 213.71 | 1: 5.32: 3: 1 | 46.91% | 13.81% |
| 73 | HAPHD | 4000 | 20 | HDI | 5.13 | 3.26 | 14.38 | Example 62 | 172 | 19.81 | DMF | 89.89 | 1: 6.10: 4.46: 0.49 | 30.43% | 21.61% |

| Examples | Method for Synthesizing Polyurethane with Carboxyl-Terminated PEG Side chain | | | | | |
|---|---|---|---|---|---|---|
| | Dehydrating Macromolecular Diol | | Prepolymerization Reaction | | Chain Extending Reaction | |
| | Temperature (°C) | Time (min) | Temperature (°C) | Time (min) | | Time (min) |
| 64 | 110 | 180 | 70 | 150 | | 20 |
| 65 | 110 | 240 | 55 | 180 | | 15 |
| 66 | 120 | 90 | 50 | 180 | | 15 |
| 67 | 100 | 180 | 70 | 60 | | 10 |
| 68 | 110 | 180 | 60 | 180 | | 20 |
| 69 | 100 | 240 | 60 | 210 | | 10 |
| 70 | 120 | 180 | 70 | 150 | | 25 |
| 71 | 110 | 150 | 80 | 120 | | 20 |
| 72 | 120 | 180 | 60 | 240 | | 30 |
| 73 | 110 | 240 | 70 | 180 | | 25 |

FIG. 19

COMB-LIKE POLYURETHANE AND METHODS FOR PREPARING AND USING THE SAME

CROSS-REFERENCE TO RELATED APPLICATIONS

This application is a continuation-in-part of International Patent Application No. PCT/CN2014/000067 with an international filing date of Jan. 20, 2014, designating the United States, now pending, and further claims priority benefits to Chinese Patent Application No. 201310123610.6 filed Apr. 10, 2013. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, and Cambridge, Mass. 02142.

BACKGROUND OF THE INVENTION

Field of the Invention

The invention relates to a comb-like polyurethane and methods for preparing and using the same.

Description of the Related Art

Polyurethane (PU) can be employed as implanted biomedical materials, however the anticoagulation property thereof cannot meet clinical requirements, and thus the biocompatibility of PU needs to be improved. As a hydrophilic, nontoxic, and non-immunogenic biocompatible material, polyethylene glycol can improve the biocompatibility of PU when grafted on the surface of a PU film.

However, typical methods to graft the polyethylene glycol involve complex processes. In addition, after the grafting reaction, no active group is available at the ends of the polyethylene glycol chains, thus limiting additional grafting.

SUMMARY OF THE INVENTION

In view of the above-described problems, it is the first objective of the invention to provide a first method for preparing a comb-like polyurethane. The method is simple and adapted to produce the comb-like polyurethane comprising a side chain of an amino-terminated or an epoxy-terminated polyethylene glycol.

It is the second objective of the invention to provide a second method for preparing a comb-like polyurethane. The method is simple and adapted to produce the comb-like polyurethane comprising a side chain of a carboxyl-terminated polyethylene glycol.

It is the third objective of the invention to provide a comb-like polyurethane prepared by the above method. An end group on the side chain of the polyethylene glycol is a reactive group. The reactive group can be employed to graft bioactive macromolecules, such as vascular endothelial growth factor (VEGF), thereby improving the adhesion and proliferation of the vascular endothelial cells on the comb-like polyurethane which can be used for vascular prostheses.

To achieve the above objective, in accordance with one embodiment of the invention, there is provided a method for preparing a comb-like polyurethane. The method comprises:
1) adding 1 part by mole of a diol having a number-average molecular weight of between 500 and 4000 to a reaction vessel, stirring and heating the diol to a temperature of between 100 and 120° C., vacuum dehydrating the diol for between 90 and 240 minutes, and cooling the diol to the temperature of between 50 and 80° C.; adding between 1.58 and 7.10 parts by mole of a diisocyanate to the diol, and pre-polymerizing the diisocyanate and the diol under vacuum at the temperature of between 50 and 80° C. for between 1 and 4 hrs to yield a polyurethane prepolymer;
2) dissolving between 0.5 and 6 parts by mole of lysine in a first solvent to yield a first solution, adding the first solution to the polyurethane prepolymer under stirring to allow chain extension for between 10 and 30 min to yield a first reaction mixture; stopping stirring and resting the first reaction mixture for between 10 and 12 hrs, pouring the first reaction mixture into water to obtain a precipitate, and drying the precipitate at room temperature to yield a polyurethane elastomer containing carboxyl groups;
3) dissolving the polyurethane elastomer containing between 0.5 and 2 parts by mole of the carboxyl groups in a second solvent to yield a second solution; adding dicyclohexylcarbodiimide and N-hydroxysuccinimide which are equimolar and are at least 1.2 times the parts by mole of the carboxyl groups in the polyurethane elastomer, and between 0.5 and 2 parts by mole of an amine-terminated polyethylene glycol in sequence to the second solution to obtain a second reaction mixture, and stirring the second reaction mixture for between 20 and 30 hrs at room temperature; and
4) adding 0.1 M hydrochloric acid which is between 1 and 3 wt. % of the second solvent to the second reaction mixture for reaction for between 3 and 6 hrs; filtering a resulting mixture to remove a precipitate from a first filtrate, and dropping the first filtrate into distilled water under stirring to form a uniformly dispersed colloid; filtering the uniformly dispersed colloid to yield a second filtrate; transferring the second filtrate to a dialysis bag having a molecular weight cutoff of between 8000 and 14000, dialyzing the second filtrate in the distilled water for between 5 and 7 days, with a water exchange every 4 to 6 hrs; vacuum freeze drying the dialyzed filtrate to yield a comb-like functional polyurethane comprising a side chain of amino-terminated polyethylene glycol;

or 1) adding 1 part by mole of a diol having a number-average molecular weight of between 500 and 4000 to a reaction vessel, stirring and heating the diol to a temperature of between 100 and 120° C., vacuum dehydrating the diol for between 90 and 240 minutes, and cooling the diol to the temperature of between 50 and 80° C.; adding between 1.58 and 7.10 parts by mole of a diisocyanate to the diol, and pre-polymerizing the diisocyanate and the diol under vacuum at the temperature of between 50 and 80° C. for between 1 and 4 hrs to yield a polyurethane prepolymer;
2) dissolving between 0.5 and 6 parts by mole of lysine in a first solvent to yield a first solution, adding the first solution to the polyurethane prepolymer under stirring to allow chain extension for between 10 and 30 min to yield a first reaction mixture; stopping stirring and resting the first reaction mixture for between 10 and 12 hrs, pouring the first reaction mixture into water to obtain a precipitate, and drying the precipitate at room temperature to yield a polyurethane elastomer containing carboxyl groups; and
3) dissolving the polyurethane elastomer containing between 1 and 4 parts by mole of carboxyl groups in a second solvent to yield a second solution, adding between 1 and 4 parts by mole of an epoxy-terminated polyethylene glycol to the second solution to obtain a second reaction mixture, heating the second reaction mixture to the temperature of between 110 and 130° C. under nitrogen protection, stirring for between 20 and 30 hrs; transferring the second reaction mixture to a dialysis bag having a molecular weight cutoff of between 8000 and 14000, dialyzing the second reaction mixture in distilled water for between 5 and 7 days, with a water exchange every 4 to 6 hrs; vacuum freeze drying a solution in the dialysis bag to yield a comb-like functional polyurethane comprising a side chain of epoxy-terminated polyethylene glycol.

A dosage of the first solvent satisfies that a solid content of the first reaction mixture is between 26 and 39 wt. %. A dosage of the second solvent satisfies that the polyurethane elastomer containing the carboxyl groups is between 2 and 10 wt. % of the second solution.

The first solvent is a mixed solvent of water and one selected from the group consisting of tetrahydrofuran, N,N-dimethylformamide, N,N-dimethylacetamide, and dimethyl sulfoxide, and a dosage of water accounts for between 10 and 30 wt. % of the mixed solvent. The second solvent is selected from N,N-dimethylformamide, N,N-dimethylacetamide, or dimethyl sulfoxide.

The number-average molecular weight of the amine-terminated polyethylene glycol or the epoxy-terminated polyethylene glycol is between 200 and 8000, and preferably between 1000 and 4000.

In accordance with another embodiment of the invention, there is provided another method for preparing a comb-like functional polyurethane. The method comprises:

1) adding 1 part by mole of a diol having a number-average molecular weight of between 500 and 4000 to a reaction vessel, stirring and heating the diol to a temperature of between 100 and 120° C., vacuum dehydrating the diol for between 90 and 240 minutes, and cooling the diol to the temperature of between 50 and 80° C.; adding between 2.2 and 7.08 parts by mole of a diisocyanate to the diol, and pre-polymerizing the diisocyanate and the diol under vacuum at the temperature of between 50 and 80° C. for between 1 and 4 hrs to yield a polyurethane prepolymer; and 2) dissolving between 0.15 and 2.10 parts by mole of a diamine chain extender containing a side chain of polyethylene glycol in tetrahydrofuran or in a second solvent, adding a resulting solution to the polyurethane prepolymer while stirring to yield a reaction system; stopping heating and allowing the reaction system to react for between 10 and 15 min; dissolving between 0.5 and 4.5 part by mole of lysine in water to form a lysine solution, and adding the lysine solution to the reaction system for chain extension for between 10 and 30 min; stopping stirring and resting the reaction mixture for between 10 and 12 hrs; transferring the reaction mixture to a dialysis bag having a molecular weight cutoff of between 8000 and 14000, dialyzing the reaction mixture in distilled water for between 5 and 7 days, with a water exchange every 4 to 6 hrs; and vacuum freeze drying a solution in the dialysis bag to yield a comb-like functional polyurethane comprising a carboxyl-terminated a side chain of polyethylene glycol.

A dosage of tetrahydrofuran or the second solvent satisfies that a total weight of the added reactants thereto is between 30 and 50 wt. % of the resulting solution, and the content of water is between 10 and 30 wt. % of the weight of the second solvent.

The second solvent is selected from N,N-dimethylformamide, N,N-dimethylacetamide, or dimethyl sulfoxide. The diamine chain extender (Lysine-NH-PEG) containing the side chain of polyethylene glycol is represented by the following formula:

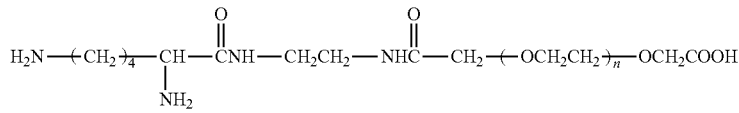

in which n represents a positive integer ranging from 4 to 180.

To prepare the diamine chain extender containing the side chain of polyethylene glycol, first, $N^{\alpha}$, $N^{\epsilon}$-bis(tert-butoxycarbonyl)-lysine and ethylenediamine are employed to prepare $N^{\alpha}$, $N^{\epsilon}$-bis(tert-butoxycarbonyl)-lysine ethylenediamine monoamide (DiBOC-Lysine-NH$_2$) by the conventional carbodiimide condensation method, and the chemical structural thereof is:

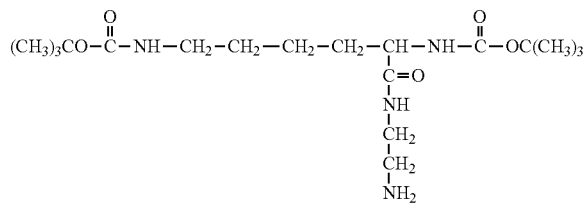

Then $N^{\alpha}$, $N^{\epsilon}$-bis(tert-butoxycarbonyl)-lysine ethylenediamine monoamide and the carboxyl-terminated polyethylene glycol are employed to prepare the diamine chain extender containing the side chain of polyethylene glycol via the conventional carbodiimide condensation method.

In accordance with still another embodiment of the invention, there is provided a comb-like functional polyurethane prepared by the above method. The comb-like functional polyurethane comprises the side chain of polyethylene glycol having a reactive end group. The reactive end group is the amino group, the epoxy group, or the carboxyl group. A typical peak of the polyethylene glycol appears on a $^1$H-NMR spectrum at a chemical shift of 3.50 ppm and on an infrared spectrum at 1110 cm$^{-1}$.

In accordance with still another embodiment of the invention, there is provided a comb-like polyurethane prepared by the above method, which has been grafted with vascular endothelial growth factor (VEGF) to selectively recruit vascular endothelial cells and to facilitate angiogenic growth of the endothelial cells (e.g. formation of vascular tube-like morphology); wherein the comb-like polyurethane comprises the side chain of polyethylene glycol having an epoxy end group; the grafting comprises an incubation of the comb-like polyurethane into VEGF aqueous solution at a concentration of between 50 and 50000 ng/mL at 37° C. for between 1 and 3 days.

Advantages according to embodiments of the invention are summarized as follows:

1) The end group of the polyethylene glycol side chain of the comb-like functional polyurethane is a reactive group such as the epoxy group, the amino group, and the carboxyl group, thereby providing a reaction site for grafting of bioactive molecules, increasing biological activity of the material, prolonging the service life of a product implanted in human body, and enlarging the application range of the polyurethane in the medical field, e.g. solving the limited antithrombogenicity problem of small-diameter vascular prostheses.

2) A mixed solvent of water and the organic solvent is employed in the method, thereby solving the insoluble problem of the lysine as an inner salt in the polyurethane solvent. Both lysine and the polyurethane can dissolve in the mixed solvent, thus lysine can be employed as a polyurethane chain extender. Meanwhile, the carboxyl group of lysine provides reaction sites for the polyurethane, thereby being convenient to graft with the polyethylene glycol. Moreover, lysine is a natural amino acid, thus polyurethane materials made from lysine are safer and more suitable to be implanted in human body than conventional polyurethanes.

3) The preparation process is different from existing methods, thereby providing a new choice for preparing the comb-like functional polyurethane comprising the side chain of polyethylene glycol.

4) The preparation process has less steps, simple operation, easy implementation, and is convenient for generalization.

in the infrared spectrum of the DiBoc-Lysine-$NH_2$: 3312 $cm^{-1}$, a stretching vibration of N—H in amide; 2976 $cm^{-1}$, 2933 $cm^{-1}$, a stretching vibration of C—H in methyl and in methylene; 1694 $cm^{-1}$, a stretching vibration of a carbonyl in amide; 1528 $cm^{-1}$, a bending vibration of N—H and a stretching vibration of the C($H_2$)—N; 1170 $cm^{-1}$, a stretching vibration of a C—O—C in carbamate. In comparison with the infrared spectrum of the DiBoc-Lysine-$NH_2$, in the infrared spectrum of the Lysine-NH-PEG: 3323 $cm^{-1}$ being wider, a stretching vibration of O—H in the carboxyl after grafting carboxyl-terminated polyethylene glycol; 1716 $cm^{-1}$, a stretching vibration of C=O in carboxyl; 1699 $cm^{-1}$, a stretching vibration of a C=O being smaller because Boc protection group has been removed; 1113 $cm^{-1}$, the strong peak being a stretching vibration of C—O—C in the polyethylene glycol chain.

Figure 4A:
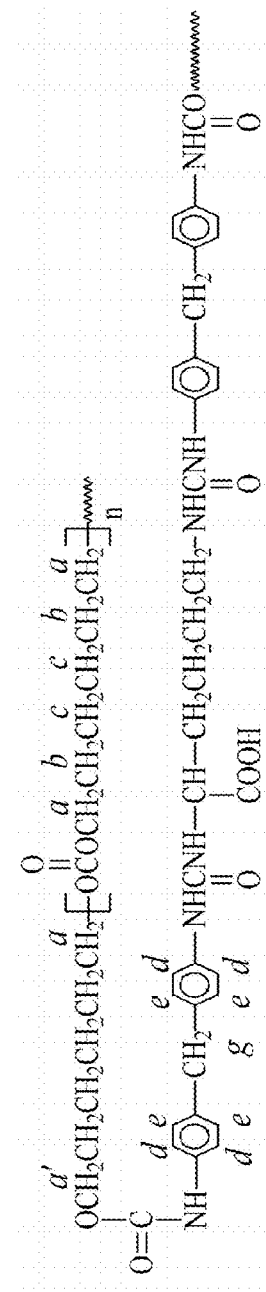
Figure 4B:
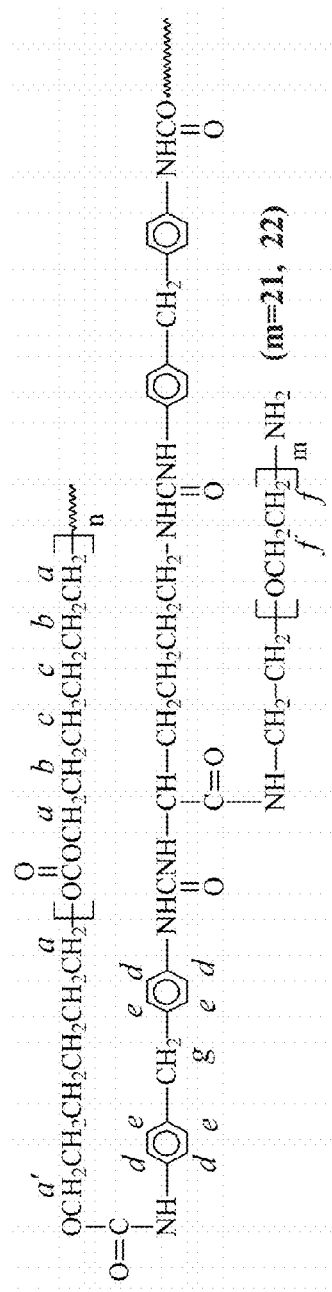
Figure 4C:
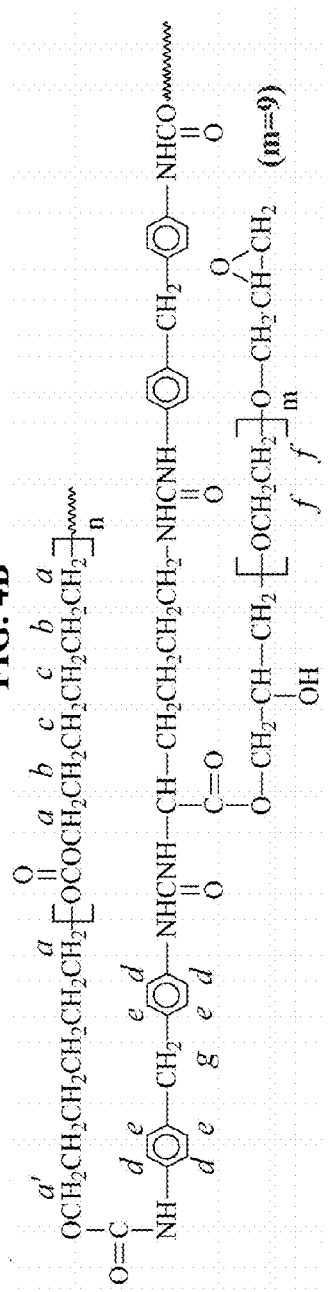

FIG. 4A is a schematic diagram of a polyurethane elastomer containing carboxyl groups prepared by example 2. FIG. 4B is a comb-like functional polyurethane comprising a side chain of amino-terminated polyethylene glycol prepared by the example 31. FIG. 4C is a comb-like functional polyurethane comprising a side chain of epoxy-terminated polyethylene glycol prepared by example 39. Some types of hydrogen in the structure are marked by italic lowercases, and assignments thereof is shown in $^1$H-NMR spectra of FIG. 5.

Figure 5:
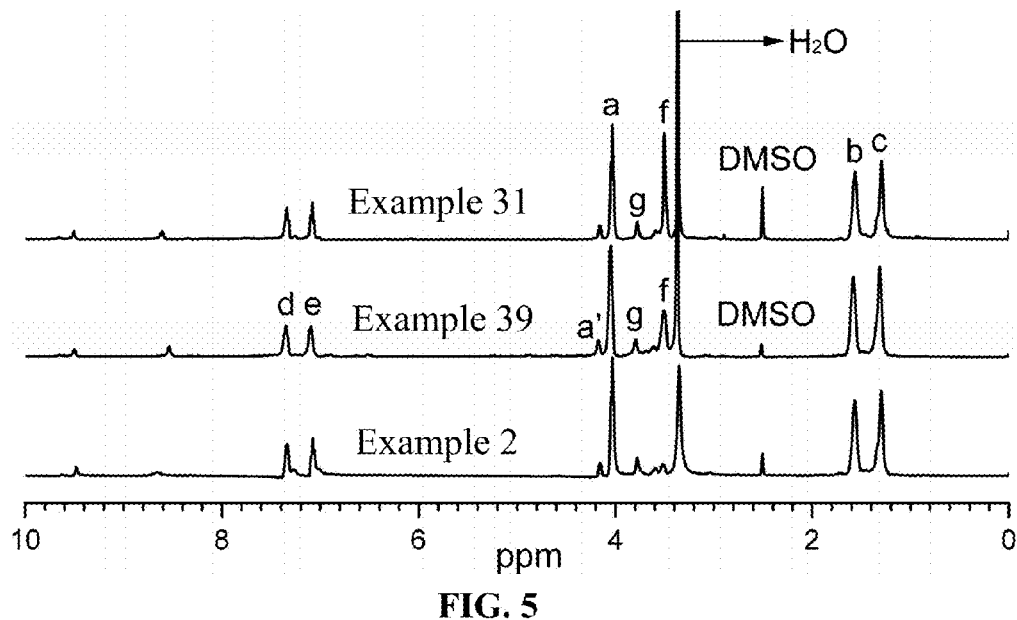

FIG. 5 is $^1$H-NMR spectra of a comb-like functional polyurethane comprising a side chain of amino-terminated polyethylene glycol prepared by the example 31, a comb-like functional polyurethane comprising a side chain of epoxy-terminated polyethylene glycol prepared by the example 39, and a polyurethane elastomer containing carboxyl groups prepared by example 2.

As known by FIGS. 4A, 4B, 4C, and 5, both soft-segment hydrogen peaks (a, b, and c) and hard-segment benzene ring hydrogen peaks (d, e, and g) appear on the spectra of three materials. However, hydrogen peak f (chemical shift is 3.51 ppm) of polyethylene glycol chains only appears in the spectra of the example 31 and 39 after grafting the polyethylene glycol side chain, meaning that polyethylene glycol has been grafted on the main chain of the polyurethane; DMSO in FIG. 5 indicates a peak from a solvent dimethyl sulfoxide; a chemical shift 3.36 ppm is a water peak in the solvent.

Figure 6:
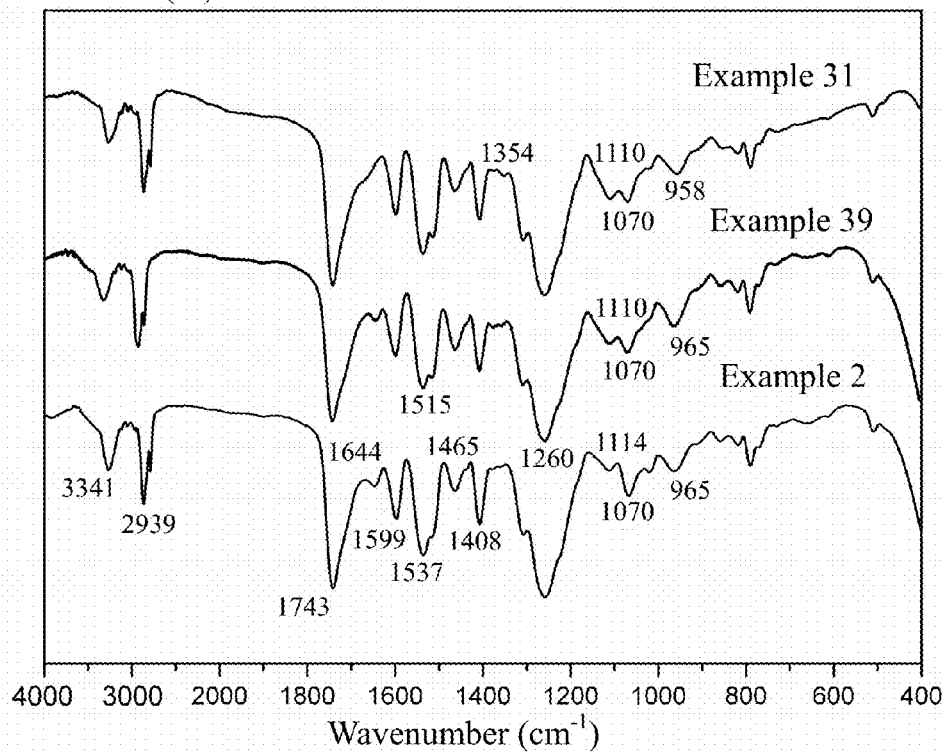

FIG. 6 is an infrared spectrum of a comb-like functional polyurethane containing a side chain of amino-terminated polyethylene glycol prepared by the example 31, a functional polyurethane containing a side chain of epoxy-terminated polyethylene glycol prepared by the example 39, and a polyurethane elastomer containing carboxyl groups prepared by example 2.

As shown by FIG. 6, infrared spectrums of the three polyurethanes are similar, and assignments of major peaks are (unit: $cm^{-1}$): 3341, a stretching vibration of hydrogen-bonded N—H in the hard-segment carbamate and urea group; 2939, a stretching vibration of —$CH_2$—; 1743, a stretching vibration of C=O in carbonate from the soft segment; 1644, a stretching vibration of hydrogen-bonded C=O in urea from the hard segment; 1599, a benzene ring skeletal vibration; 1537, a bending vibration of N—H and a stretching vibration of C—N; 1465, a bending vibration of —$CH_2$—; 1408, a benzene ring C—C vibration; 1260, a stretching vibration of C—O—C in carbonate from the soft segment; 1114 (example 2), a stretching vibration of C($H_2$)—O, from carbonate and carbamate groups; 1110 (examples 31 and 39), a stretching vibration of C($H_2$)—O in ether bond from the polyethylene glycol; 1070, from a C—O—C in the carbamate. In comparison with the spectrum of example 2, a 1110 $cm^{-1}$ stretching vibration of C($H_2$)—O from the polyethylene glycol appears on the spectrum of examples 31, 39, overlapping the original 1114 $cm^{-1}$ peak (example 2), and the intensity of the mixed peak in comparison with the adjacent 1070 $cm^{-1}$ obviously increases; in addition, peak intensity at 1644 $cm^{-1}$ of the examples 31, 39 obviously reduces, because the hydrogen bond among hard-segment urea groups is weakened after grafting a polyethylene glycol side chain.

Figure 7A:
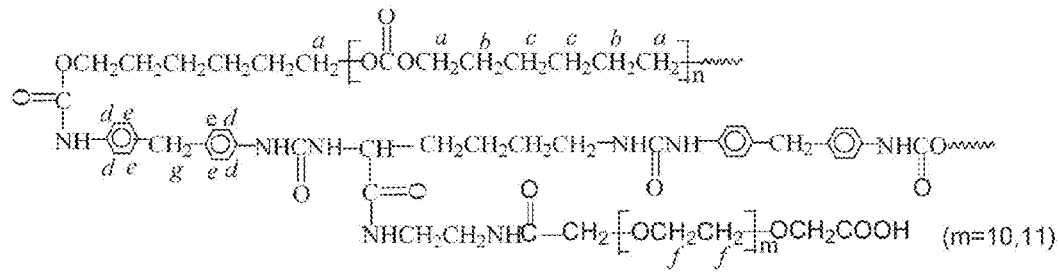
Figure 7B:
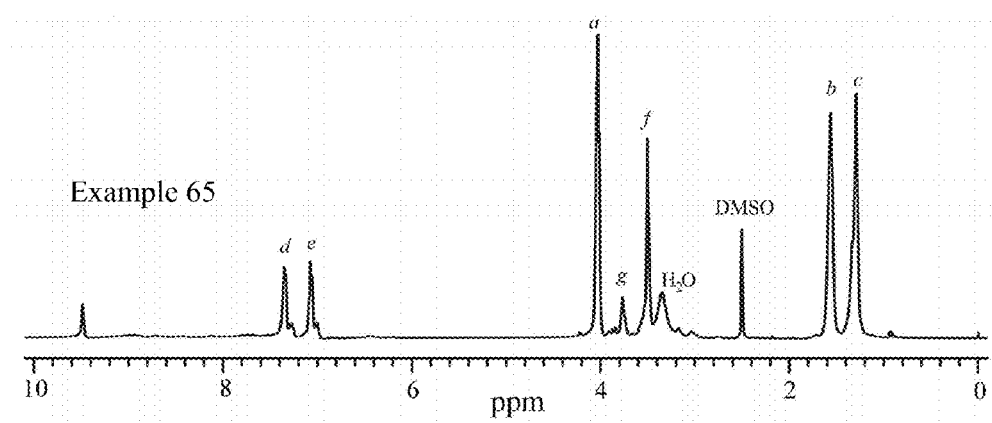

FIGS. 7A and 7B are schematic diagram and a $^1$H-NMR spectrum of a functional polyurethane with a carboxyl-terminated polyethylene glycol side chain prepared by the example 65; a characteristic hydrogen peak of a polyethylene glycol chain appears at chemical shift of 3.50 ppm.

Figure 8:
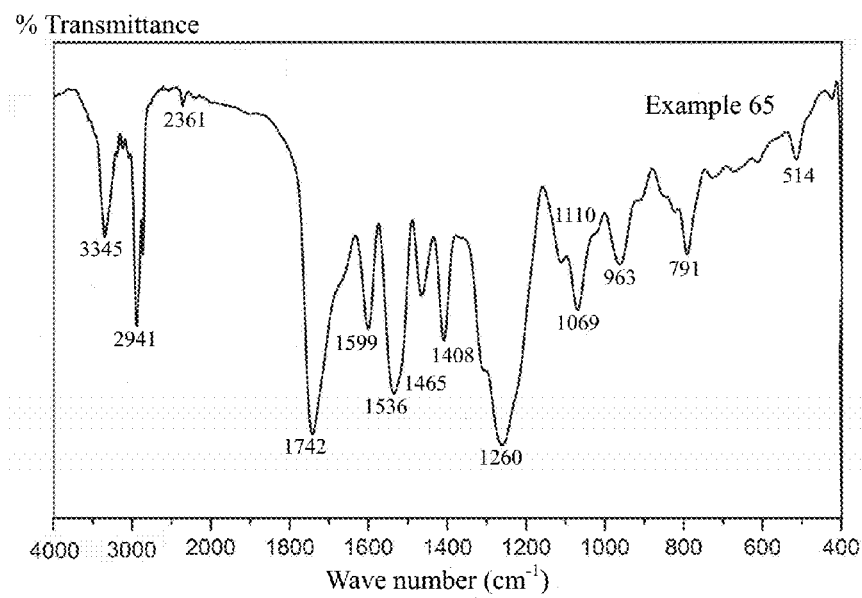

FIG. 8 is an infrared spectrum of a functional polyurethane with a carboxyl-terminated polyethylene glycol side chain prepared by the example 65; assignments of peaks in the FIG. 8 are the same as those of FIG. 6; absorption peak of ether bond in the polyethylene glycol appears at 1110 $cm^{-1}$.

Figure 9:
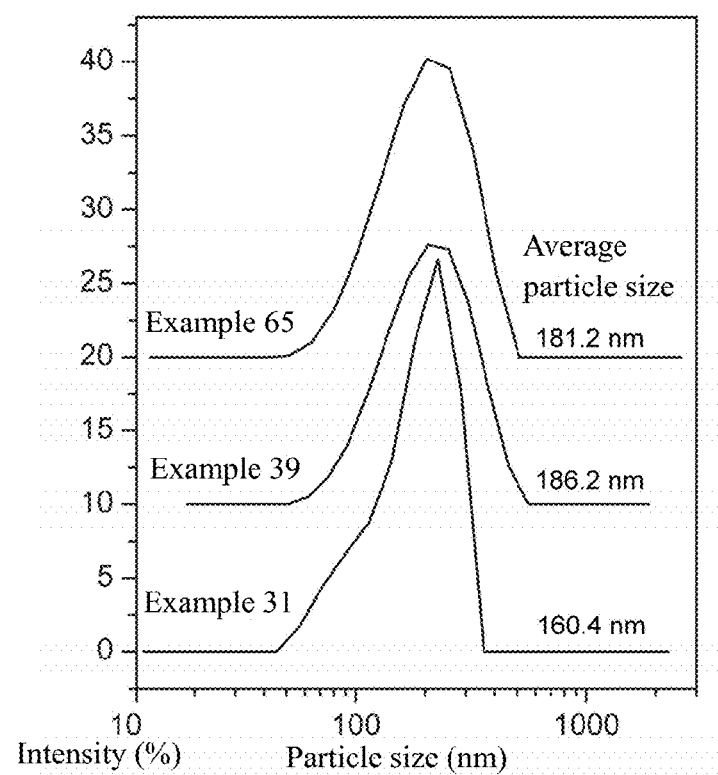

FIG. 9 is a particle size distribution diagram of hydrocolloids of functional polyurethanes with amino-, epoxy-, carboxyl-terminated polyethylene glycol side chains prepared by example 31, example 39, and example 65, respectively.

Figure 10:
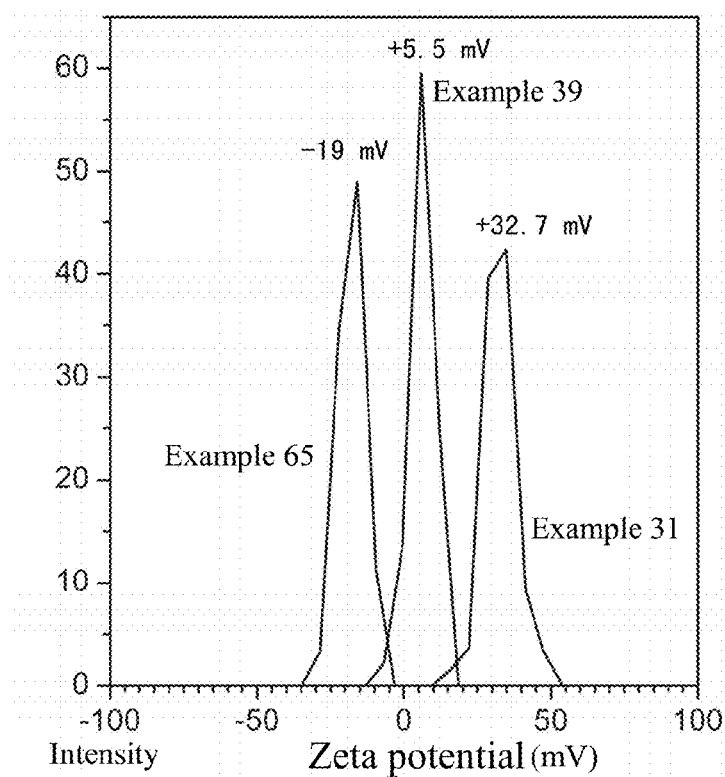

FIG. 10 is a Zeta potential distribution diagram of hydrocolloids of functional polyurethanes with amino-, epoxy-, carboxyl-terminated polyethylene glycol side chains prepared by example 31, example 39, and example 65, respectively.

As shown by FIGS. 9-10, the average particle sizes of the three colloids are less than 200 nm, and the colloid carrying amino groups in a phosphate buffered saline (pH=7.4) is positively charged (Zeta potential is +32.7 mV, Example 31), because of the ionization of amino group to form ammonium group. The colloid carrying epoxy groups is tested to be weakly positively charged (Zeta potential is +5.5 mV, Example 39) rather than being electro neutrality, because the polyethylene glycol chain absorbs a small quantity of positive ions. The colloid carrying carboxyl groups is negatively charged (Zeta potential is −19 mV, Example 65), because the carboxyl groups can ionize to form carboxylate anions.

Figure 11:
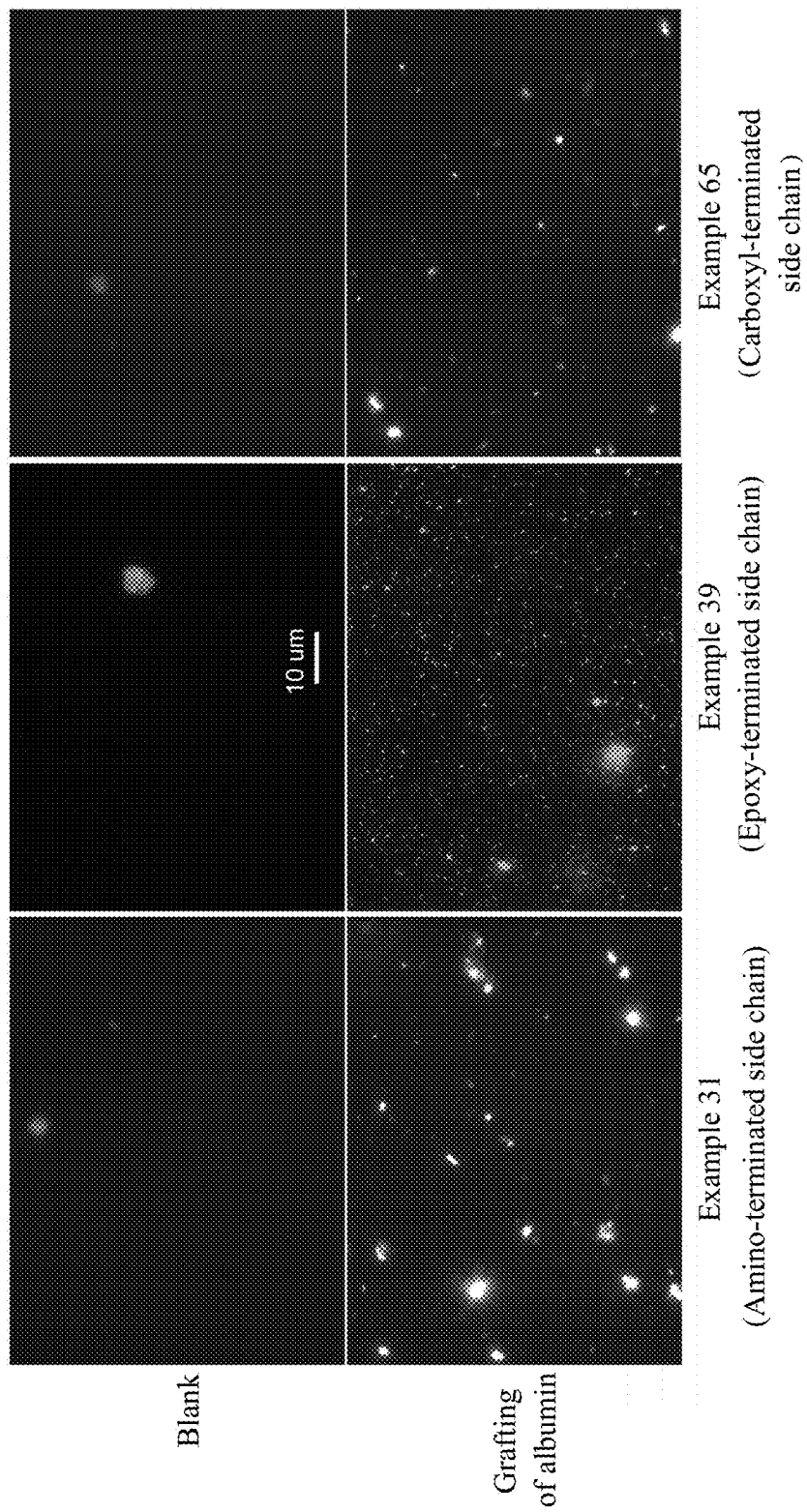

FIG. 11 is a 1000× fluorescent micrograph of albumin-grafted functional polyurethane hydrocolloid and a corresponding blank hydrocolloid prepared by examples 31, 39, and 65; scale bar is 10 μm.

As shown by the micrograph, the blank colloids display weak autofluorescence under the fluorescent microscope, and only particles with large sizes can be seen. Samples grafted with fluorescence-labeled albumin emit strong fluorescence, making both small and large particles clearly visible. The micrograph shows that the functional polyurethanes prepared by the invention has reactive groups, can react with biomolecules such as albumin, providing possibility for further biological modifications.

Figure 12:
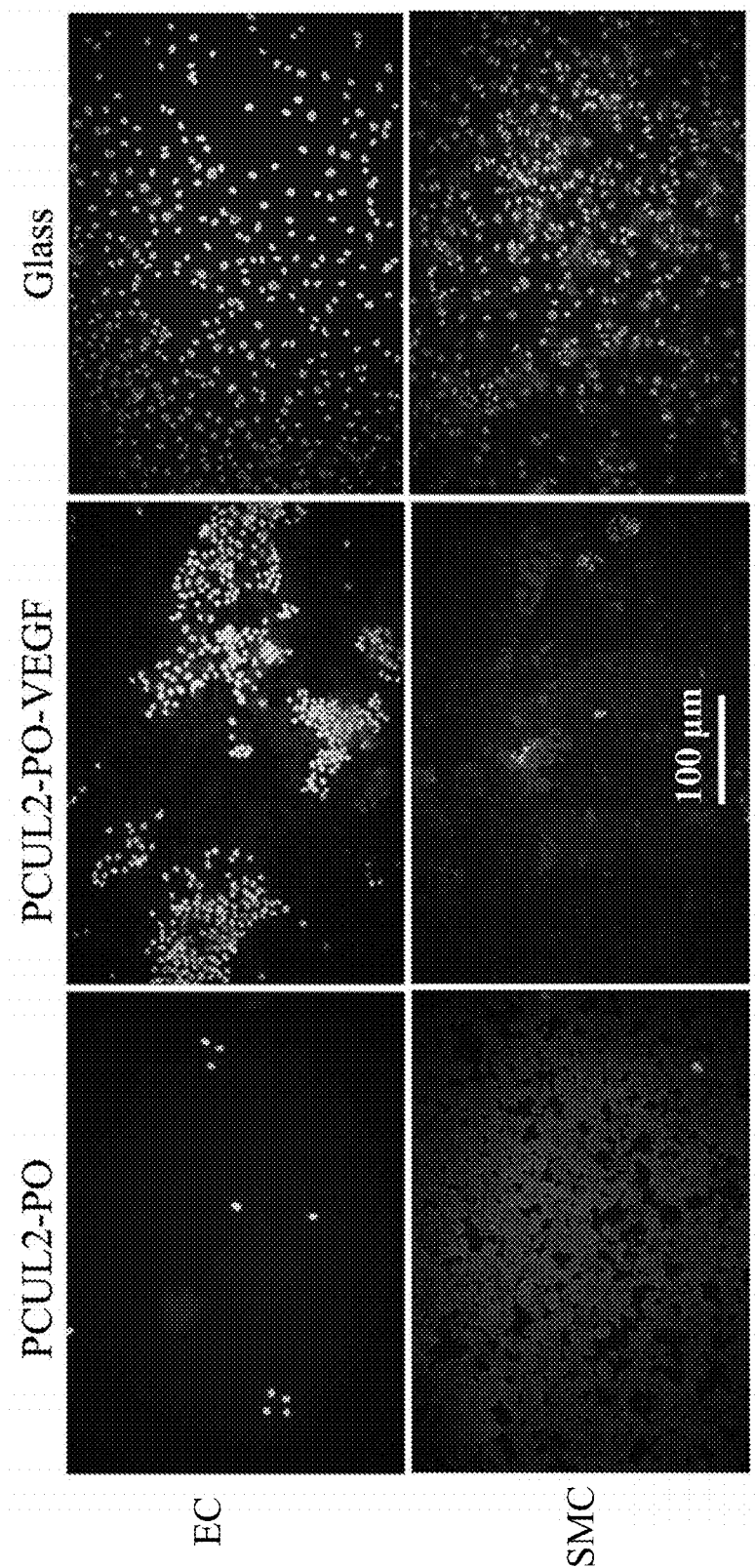

FIG. 12 is Hoechst stained cells on PCUL2-PO (Example 39) films 10 h post cell seeding. Endothelial cell (EC) density is much higher on VEGF-grafted PCUL2-PO (PCUL2-PO-VEGF) than on bare PCUL2-PO. Smooth muscle cells (SMCs) adhere poorly to both materials. ECs and SMCs adhere to control glasses.

Figure 13:
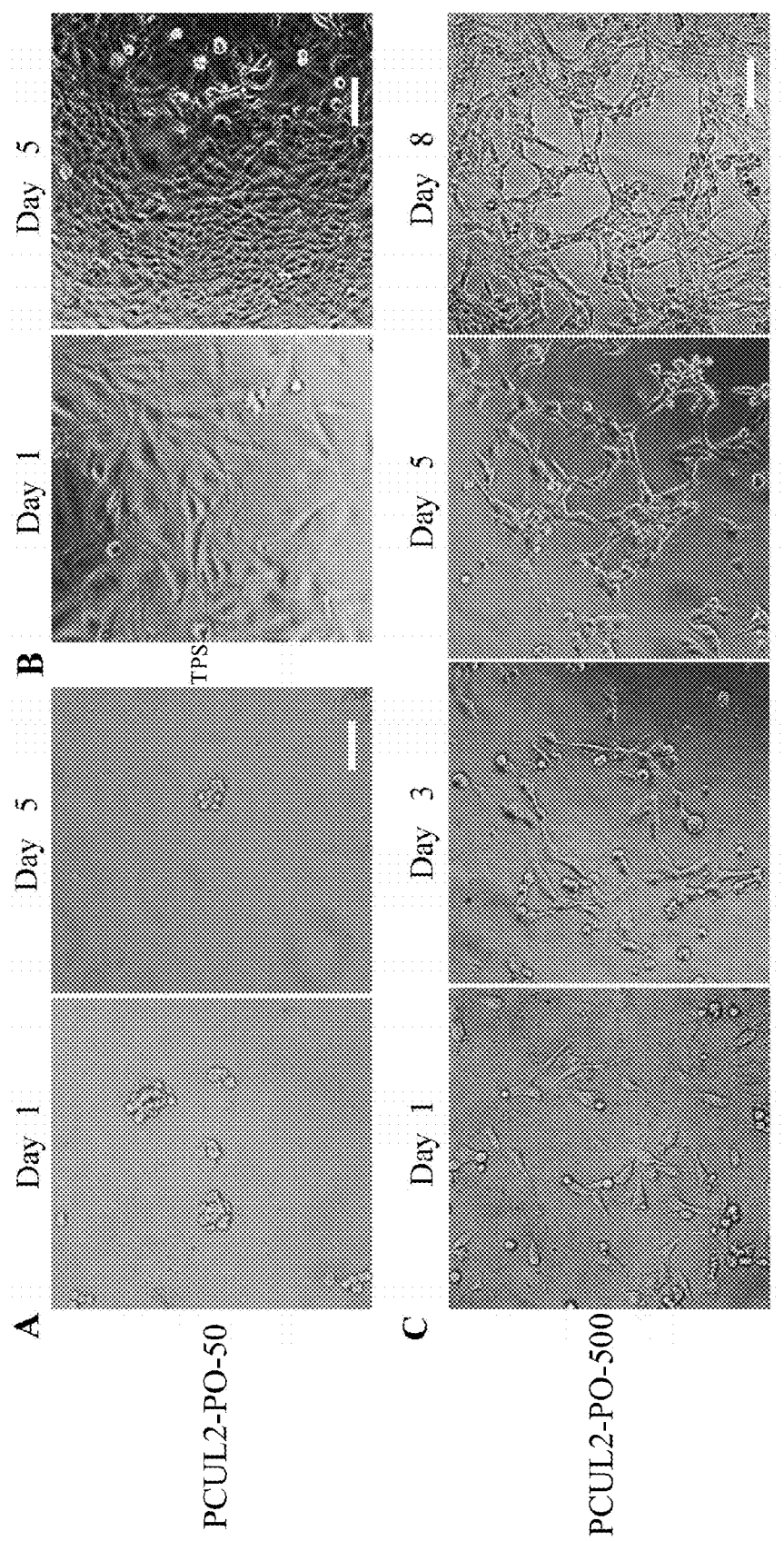

FIG. 13 is a morphological evolution of human umbilical vein endothelial cells (HUVECs) on VEGF-grafted PCUL2-PO films. Scale bars: 100 μm. (A) Films treated with VEGF at 50 ng/mL (PCUL2-PO-50) show a few individual cells and cell clusters and the number of cells obviously decreases with time. The cell morphology and density on PCUL2-PO-0 (without VEGF grafting) is similar to that on PCUL2-PO-50. (B) Tissue culture polystyrene (TPS) control induces well-spread cells, reaching confluence in 5 days. (C) PCUL2-PO-500 films induce extensive vascular tube formation after 8 days.

FIG. 14 shows types and contents of materials for preparing a polyurethane elastomer containing carboxyl groups in examples 1-30, in which, the following abbreviations are used: PCD: polycarbonate diol; PTMG: polytetramethylene glycol diol; PCL: polycaprolactone diol; PPG: polypropylene glycol diol; HAPHD: polyhexamethylene adipate; MDI: 4,4'-diphenylmethane diisocyanate; HDI: 1,6-hexamethylene diisocyanate; TDI: 2,4-toluene diisocyanate or 2,6-toluene diisocyanate; IPDI: isophorone diisocyanate; LDI: lysine ethyl ester diisocynanate; THF: tetrahydrofuran; DMF: N,N-dimethylformamide; DMAc: N,N-dimethylacetamide; and DMSO: dimethyl sulfoxide; and the molar ratio is the ratio of macromolecular diol:diisocyanate:lysine.

FIG. 15 shows process parameters for preparing a polyurethane elastomer containing carboxyl groups in examples 1-30, in which the carboxyl equivalent equals the mole number of the lysine divided by the total weight of the polymer.

FIG. 16 shows types and contents of materials and process parameters for preparing a comb-like functional polyurethane comprising an amino-terminated or a epoxy-terminated polyethylene glycol side chain in examples 31-46; in which, the following abbreviations are used: PEG: polyethylene glycol; PN: polyethylene glycol diamine; PO: polyethylene glycol diglycidyl ether; THF: tetrahydrofuran; DMF: N,N-dimethylformamide; DMAc: N,N-dimethylacetamide; DMSO: dimethyl sulfoxide.

FIG. 17 shows materials for preparing a diamine chain extender (Lysine-NH-PEG) comprising a side chain of polyethylene glycol in examples 48-63, in which, the following abbreviations are used: NHS: N-hydroxysuccinimide; DCC: dicyclohexylcarbodiimide; PEG: bifunctionalized carboxyl-terminated polyethylene glycol; and n represents a number of repeated structure units of bifunctionalized carboxyl-terminated polyethylene glycol or products.

FIG. 18 shows types and contents of materials for preparing a comb-like functional polyurethane comprising a carboxyl-terminated polyethylene glycol side chain in examples 64-73, in which, the following abbreviations are used: PCD: polycarbonate diols; PTMG: polymethylene glycol diol; PCL: polycaprolactone diol; PPG: polypropylene glycol diol; HAPHD: polyhexamethylene adipate; MDI: 4,4'-diphenylmethane diisocyanate; HDI: 1,6-hexamethylene diisocyanate; TDI: 2,4-toluene diisocyanate or 2,6-toluene diisocyanate; IPDI: isophorone diisocyanate; LDI: lysine ethyl ester diisocynanate; THF: tetrahydrofuran; DMF: N,N-dimethylformamide; DMAc: N,N-dimethylacetamide; DMSO: dimethyl sulfoxide; n is a number of repeating units of the polyethylene glycol (PEG) chain in Lysine-NH-PEG; and the molar ratio is the ratio of macromolecular diol:diisocyanate:lysine:Lysine-NH-PEG FIG. 19 shows process parameters for preparing a comb-like functional polyurethane comprising a carboxyl-terminated polyethylene glycol side chain in examples 64-73.

DETAILED DESCRIPTION OF THE EMBODIMENTS

For further illustrating the invention, experiments detailing a comb-like functional polyurethane and a method for preparing the same are described below. It should be noted that the following examples are intended to describe and not to limit the invention.

In addition, it is worth mentioning that examples of the comb-like functional polyurethane material with epoxy- or amino-terminated polyethylene glycol side chain are given respectively in accordance with the steps in the method, namely, examples 1-30 are in accordance with the step 1) and step 2) for preparing a polyurethane elastomer containing carboxyl groups on the main chain. Examples 31-37 are in accordance with the step 3) and step 4) for preparing the comb-like functional polyurethane with amino-terminated polyethylene glycol side chain. Examples 38-46 are in accordance with the step 3) for preparing the comb-like functional polyurethane material with epoxy-terminated polyethylene glycol side chain.

Examples 1-30

This group of examples are to prepare a polyurethane elastomer containing carboxyl groups on the main chain.

1) 1 part by mole of a macromolecular diol was put into a reaction vessel, and stirred and heated. The diol was then dehydrated under vacuum and cooled. Thereafter, diisocyanate was added to the diol for prepolymerization to yield a polyurethane prepolymer at the kept temperature under vacuum.

2) Lysine was dissolved in a first solvent to yield a first solution. The first solution was added to the polyurethane prepolymer while stirring for chain extending reaction for certain time. A resulting reaction mixture was stood for 10-12 hours, and then poured into water for precipitation. A precipitate was thereafter dried at room temperature to yield a polyurethane elastomer containing carboxyl groups.

Types and contents of the materials employed in each example are shown in FIG. 14, and parameters of the preparation process are shown in FIG. 15.

Examples 31-37

This group of examples are to prepare a comb-like functional polyurethane with amino-terminated polyethylene glycol side chain via the polyurethane elastomer containing the carboxyl groups prepared by the examples 1-30.

1) The polyurethane elastomer containing the carboxyl groups was putted into a second solvent, then dicyclohexylcarbodiimide (DCC, a molecular weight was 206.33) and N-hydroxysuccinimide (NHS, a molecular weight was 115.03) which were equimolar and were 1.2 times as the mole as the carboxyl in the polyurethane elastomer in examples 31-36 and 1.3 times in example 37, and an amine-terminated polyethylene glycol was added in sequence, and stirred at room temperature to yield a reaction solution. Taking the example 31, for instance, to calculate the specific addition of DCC and NHC: molar weight of DCC was the weight of polyurethane in FIG. 16 times the carboxyl equivalent of the polyurethane in FIG. 15 times 1.2, which was, 0.78×0.642×1.2=0.601 mmol, that was 0.124 g; similarly, NHS was calculated to be 0.069 g. DCC and NHC in other examples can also be calculated in the same way. The molar weight of the DCC and the NHC in the example 37 were 1.3 times as the molar weight as the carboxyl in the polyurethane elastomer, thus molar weight of the DCC is the weight of polyurethane in FIG. 16 times the carboxyl equivalent of the polyurethane in FIG. 15 times 1.3, which was, 2.42×0.828×1.3=2.605 mmol, that was 0.537 g; similarly, NHS was calculated to be 0.781 g.

2) 0.1 M dilute hydrochloric acid which was 1 wt. % of the weight of the second solvent was added to the reaction solution for reaction for 3 hrs in the examples 31-36. 0.1 M dilute hydrochloric acid which was 3 wt. % of the weight of the second solvent was added to the reaction solution for reaction for 6 hrs in the example 37. A resulting mixture was filtered to remove a precipitate from a first filtrate. The first filtrate was dropped into distilled water under stirring to form a uniformly dispersed colloid. The uniformly dispersed colloid was filtered to yield a second filtrate. The second filtrate was then put into a dialysis bag having a molecular weight cutoff of between 8000 and 14000 and dialyzed in the distilled water. The distilled water was changed every 4 to 6 hrs. After between 5 and 7 days of dialysis, the dialysis bag was taken out, and a solution in the dialysis bag was then vacuum freeze dried to yield a comb-like functional polyurethane comprising a side chain of amino-terminated polyethylene glycol.

Types and contents of the materials employed in each example and parameters of the preparation process are shown in FIG. 16.

Examples 38-46

This group of examples are to prepare a comb-like functional polyurethane with an epoxy-terminated polyethylene glycol side chain via a polyurethane elastomer containing carboxyl groups prepared by the examples 1-30.

The polyurethane elastomer containing the carboxyl groups was dissolved in a second solvent to yield a second solution. Thereafter, an epoxy-terminated polyethylene glycol was then added to the second solution. A resulting mixture was heated under nitrogen protection, and stirred for reaction. Thereafter, a reaction mixture was put into a dialysis bag having a molecular weight cutoff of between 8000 and 14000 and dialyzed in the distilled water. The distilled water was changed every 4 to 6 hrs. After between 5 and 7 days of dialysis, the dialysis bag was taken out, and a solution in the dialysis bag was then vacuum freeze dried to yield a comb-like functional polyurethane comprising an epoxy-terminated polyethylene glycol side chain.

Types and contents of the materials employed in each example and parameters of the preparation process are shown in FIG. 16.

Example 47

This example is to prepare $N^{\alpha},N^{\epsilon}$,-di-(tert-butoxycarbonyl)-lysine ethylenediamine monoamide (DiBoc-Lysine-$NH_2$).

Figure 1:
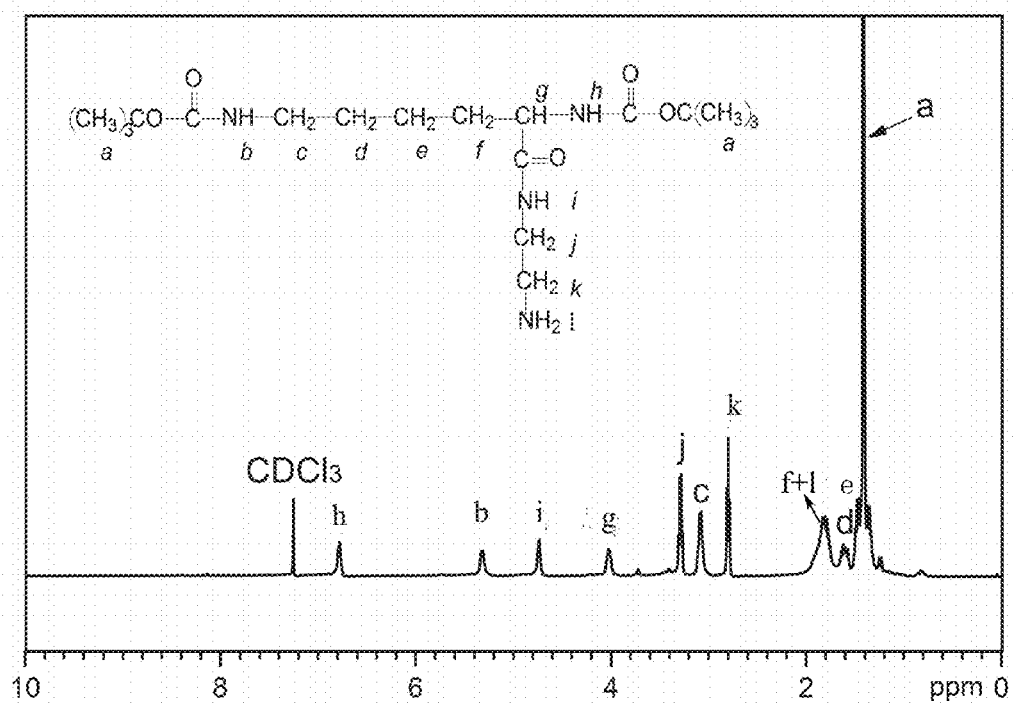
FIG. 1 is a schematic diagram of DiBoc-Lysine-$NH_2$ prepared by the example 47; all types of hydrogen in the structure are marked by lowercases, and assignments thereof are shown in a $^1$H-NMR spectrum.
Figure 2:
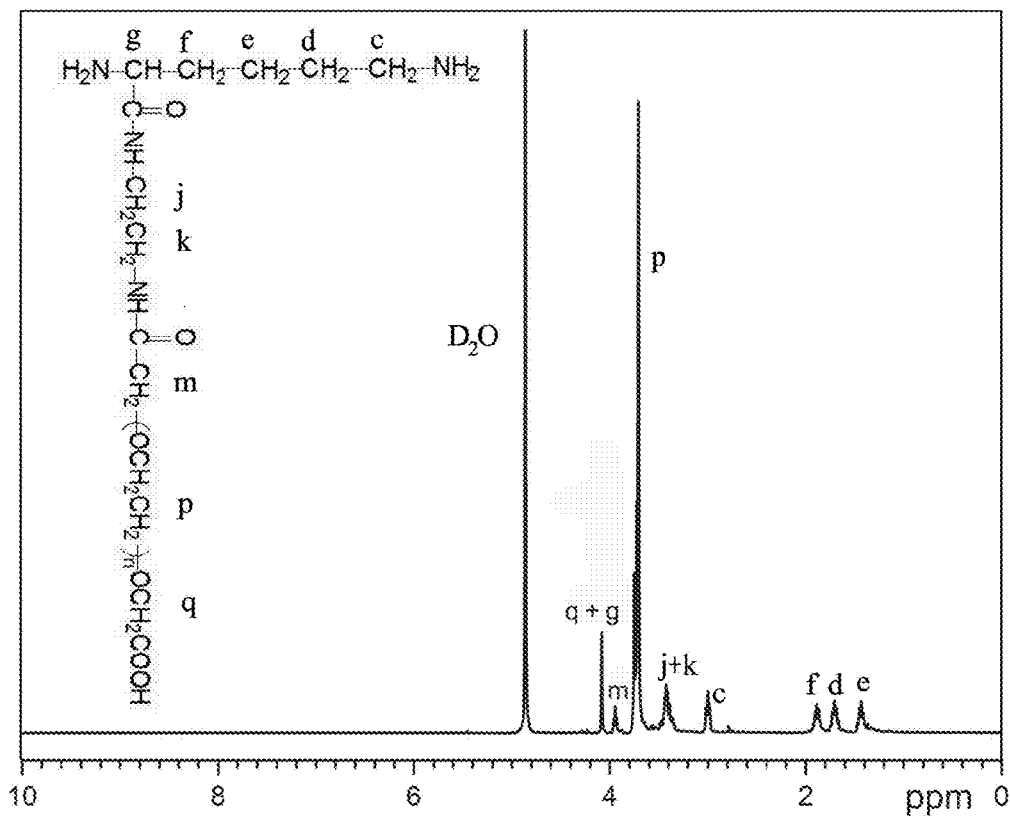
FIG. 2 is a schematic diagram of Lysine-NH-PEG prepared by the example 49; all types of hydrogen in the structure are marked by lowercases, and assignments thereof are shown in a $^1$H-NMR spectrum.
Figure 3:
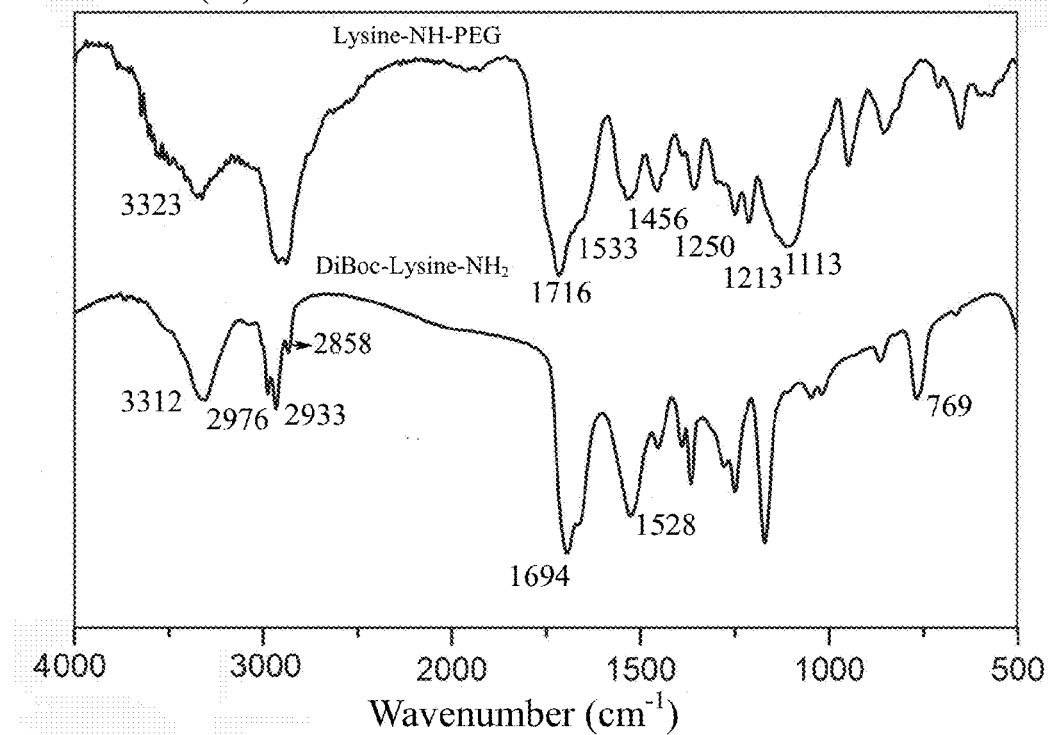
FIG. 3 is an infrared spectrum of DiBoc-Lysine-$NH_2$ prepared by the example 47 and Lysine-NH-PEG prepared by the example 49; as shown by the FIG. 3, the infrared spectrum of the two materials are similar, and assignments of major peaks thereof are as follows.

10.5 g $N^{\alpha},N^{\epsilon}$,-di-(tert-butoxycarbonyl)-lysine (30 mmol, provided by Aldrich company) was dissolved in 60 mL of chloroform. 3.48 g NHS (30 mmol) was added to a resulting solution and stirred for reaction for half an hour. 9.3 g DCC (45 mmol) was then added for continuing reaction for 2 hrs. A large quantity of white precipitate produced in the reaction was dicyclohexylurea (DCU), and DCU was separated by filtration. A filtrate was instilled into 60 mL chloroform dissolving 4.5 g ethylenediamine, and stirred for reaction for 48 hrs. A reaction mixture was then filtered. 60 mL distilled water was added into a resulting filtrate and stirred for at least 30 minutes, then was put into a separatory funnel for phase separation, and an organic phase was separated from an aqueous phase. The organic phase was extracted by distilled water for three times and the aqueous phase was abandoned. 50 mL distilled water was added to the organic phase while stirring to yield a mixture, then the pH of the mixture was adjust to 3 using hydrochloride solution (pH=1), and stirred for 30 minutes and a white precipitate was filtered when appeared. A resulting filtrate was stood for phase separation and an aqueous phase was kept. Then, the organic phase was extracted with water for three times in the same way, and all the prepared aqueous phases were then combined. 60 mL chloroform was added into the combined aqueous phase, and stirred and adjusted the pH to 11 by a NaOH solution. The mixture was stirred for at least one hour and was stood for phase separation. The organic phase was collected. The aqueous phase was extracted with chloroform for multiple times and the organic phase was also collected. All the collected organic phases were combined and 60 g anhydrous sodium sulfate was added for drying overnight. The next day, the chloroform solution was filtered to remove sodium sulfate, and chloroform was further removed by rotary evaporation at 40-50° C. A resulting product was thereafter vacuum dried at 60° C. for 24 hrs to yield DiBoc-Lysine-$NH_2$ as a yellow solid (the yield thereof was 56%). The schematic diagram and the $^1$H-NMR spectrum thereof are shown by FIG. 1, and the infrared spectrum thereof is shown by FIG. 3.

Examples 48-63

This group of examples are to prepare a diamine chain extender (Lysine-NH-PEG) comprising a side chain of polyethylene glycol.

According to the formulations in FIG. 17, the bifunctional carboxyl-terminated polyethylene glycol (PEG) and the DiBoc-Lysine-$NH_2$ prepared by the example 47 were fully dissolved in distilled THF at room temperature. The mole number of the PEG was 2 times as that of the DiBoc-Lysine- NH$_2$, and NHS with equal molar weight as that of the carboxyl-terminated PEG was added, after half an hour, DCC with a molar weight being 1.5 times as that of the NHS was added and stirred for 48 hrs. A reaction mixture was then filtered to separate a DCU precipitate from a filtrate. The filtrate was rotary evaporated to remove a solvent, and a result product was then dissolved in chloroform to form a chloroform solution. Thereafter, 0.1 M hydrochloride solvent was instilled into the chloroform solution to adjust the pH to 3, the resulting chloroform solution was stirred for 2 hrs, and an organic phase was collected. The organic phase was dehydrated by anhydrous sodium sulfate and stirred overnight. A resulting mixture was then filtered to separate a filtrate. The filtrate was thereafter rotary evaporated to remove a solvent. A resulting product was treated by a silica gel column by using chloroform and methanol as eluting agents to yield the DiBoc-Lysine-NH-PEG. To remove the butoxycarbonyl (BOC) protection group, DiBoc-Lysine-NH-PEG was dissolved in predetermined amount of dichloromethane. Trifluoroacetic acid in a predetermined amount was then added to a resulting solution and stirred for 24 hrs at room temperature. The solvent was removed by rotary evaporation at 60° C. Finally, the Lysine-NH-PEG was yielded by drying at 80° C. for 24 hrs in a vacuum oven. The schematic diagram and the $^1$H-NMR spectrum thereof are shown by FIG. 1, and the infrared spectrum thereof is shown by FIG. 3.

Examples 64-73

This group of examples are to prepare a comb-like functional polyurethane with a carboxyl-terminated polyethylene glycol side chain.

1) A macromolecular diol was put into a reaction vessel, stirred, and heated. The diol was vacuum dehydrated and then cooled. Diisocyanate was added to the diol for prepolymerization under vacuum to yield a polyurethane prepolymer.

2) The diamine chain extender with PEG side chain prepared by the examples 48-63 were dissolved in THF or the second solvent to yield a solution and then the solution was added to the polyurethane prepolymer, and the heating was stopped for reaction for 10 minutes in examples 64-67, for 13 minutes in examples 68, 69, 73, and for 15 minutes in examples 70-72. Thereafter, lysine was dissolved in water and a lysine solution was then added to the above reaction system for a chain extending reaction. A reaction mixture was stood for between 10 and 12 hrs after the reaction, and the reaction mixture was dropped into distilled water under stirring to form a uniformly dispersed colloid. The uniformly dispersed colloid was then filtered to yield a filtrate. The filtrate was thereafter put into a dialysis bag having a molecular weight cutoff of 8000-14000 to dialyze in distilled water. The distilled water was changed every 4-6 hrs, and the dialysis bag was taken out after 5-7 days (a specific period is determined according to the overdose of raw materials in the filtrate). A solution in the dialysis bag was then vacuum freeze dried to yield a comb-like functional polyurethane comprising a carboxyl-terminated polyethylene glycol side chain.

Types and contents of the materials employed in each example are shown in FIG. 18, and parameters of the preparation process are shown in FIG. 19.

To study the structure of the comb-like functional polyurethane material, the structures are verified by instrumental analyses, and the results are shown by FIGS. 4A, 4B, 4C, 5-6, 7A, 7B, and 8 respectively.

To prepare a colloid of the functional polyurethane for grafting albumin, 0.1 g comb-like functional polyurethane material prepared by the example 31, 39, and 65 respectively were respectively dissolved in 5 mL of N, N-dimethylformamide to yield solutions. 20 mL distilled water was dropped to each solution while stirring to form the colloid. The colloid was filtered. A filtrate was then put into a dialysis bag and dialyzed in the instilled water for 5 days. The instilled water was changed every four hrs. Thus the solvent was totally removed. Thereafter, a resulting product in the dialysis bag was rotary evaporated at 50° C. to concentrate the colloid to 5 mL, thereby yielding a 2 wt. % colloid solution. A small amount of the colloid was diluted to a concentration of 0.5 wt. %, and particle sizes and the Zeta potentials of the colloids were measured (by a Malvern 3000 HSa Zetasizer). The results are shown by FIGS. 9-10.

Application Example 1

This example is to prepare an albumin-grafted colloid from the comb-like functional polyurethane with an epoxy-terminated polyethylene glycol side chain.

Fluorescein isothiocyanate-labeled pig albumin (Sigma) in 50 mM phosphate buffered solution (PBS) (pH 7.4, 1 mg/mL) was used as a model protein. In a 2-mL brown glass vial, 0.6 mL of PBS (50 mM, pH 7.4), 0.2 mL of the polyurethane colloid prepared from the polyurethane of example 39, (PCUL2-PO colloid, 2%, w/v) and 0.2 mL of fluorescein isothiocyanate-albumin were added and magnetically stirred for 30 h. The resulting colloid was centrifuged at 13000 rpm and resuspended in 0.8 mL of PBS under stirring. This washing process was repeated 6 times to remove free proteins. Finally, the colloid solution was centrifuged again and resuspended in 0.2 mL of PBS for fluorescence light microscopy. In addition, the solution of mere colloid in PBS served as a blank control (0.8 mL PBS and 0.2 mL PCUL2-PO colloid were added into the brown glass vial and were stirred and treated in the same way.) The results are shown by FIG. 11.

Application Example 2

This example is to prepare an albumin grafted colloid from the comb-like functional polyurethane with a carboxyl- or amino-terminated polyethylene glycol side chain.

Tetramethylrhodamine isothiocyanate-labeled pig albumin (Sigma) in 50 mM PBS solution (1 mg/mL, pH 7.4) was used as a model protein. Water-soluble 1-ethyl-(3-dimethylaminopropyl) carbodiimide hydrochloride (EDC) and N-hydroxysuccinimide are employed as a condensing agent. In a 2-mL brown glass vial, 0.6 mL of PBS (50 mM, pH 7.4), 0.2 mL of the polyurethane colloid (from example 31 or 65, 2%, w/v) and 0.2 mL of tetramethylrhodamine isothiocyanate-albumin were added and magnetically stirred for 30 h. The resulting colloid was centrifuged at 13000 rpm and resuspended in 0.8 mL of PBS under stirring. This washing process was repeated 6 times to remove free proteins. Finally, the colloid solution was centrifuged again and resuspended in 0.2 mL of PBS for fluorescence light microscopy. In addition, the solution of mere colloid in PBS served as a blank control (0.8 mL PBS and 0.2 mL the functional polyurethane colloid were added into the brown glass vial and were stirred and treated in the same way). The results are shown by FIG. 11.

Application Example 3

This example employs Endothelial Vascular Growth Factor (VEGF) to graft comb-like functional polyurethane with a epoxy-terminated polyethylene glycol side chain (in the example 39, noted as PCUL2-PO), so as to verify that VEGF-grafted PCUL2-PO can selectively recruit endothelial cells.

PCUL2-PO (the polyurethane from example 39) was dissolved in dimethylformamide (DMF) at a concentration of 2 wt. % and 130 μL was spread onto an alcohol-rinsed cover glass with a diameter of 13 mm. The coating was dried at 50° C. for 24 h, followed by vacuum drying at 80° C. for another 30 h. Another side of the glass cover was also coated with PCUL2-PO using the same method. Test films were sterilized by ethylene oxide and conditioned in sterile water at 37° C. for 24 h to equilibrate their surface composition prior to VEGF grafting.

Glass covers with PCUL2-PO film on both sides were put into wells of a 24-well plate and incubated in 200 μL of VEGF 165 (Perprotech, USA) solution at 1.25 μg/mL, corresponding to 0.25 μg per well (n=3). After incubation at 37° C. for 40 h, the VEGF concentration in each supernatant was measured using an enzyme-linked immunosorbent assay (ELISA) kit (Perprotech, USA) for VEGF 165 according to manufacturer's instructions.

The amount of bound VEGF on the test film was calculated as $75.1 \pm 4.9$ ng/cm$^2$ with the following stipulations: 1) physical adsorption onto the well bottom made of tissue culture polystyrene (TPS) was not taken into consideration; and 2) it was assumed that VEGF was uniformly grafted on both sides of the test film.

VEGF-treated PCUL2-PO, designated as PCUL2-PO-VEGF was used to investigate cell selectivity. The same film without VEGF treatment and blank glasses served as controls. Human umbilical vein endothelial cells (HUVECs, from West China Centre of Medical Sciences, Sichuan University, China) were target cells while Human umbilical vein smooth muscle cells (HUVSMCs, from ScienCell, USA) served as interfering cells. To investigate cell adhesion, $10^5$ HUVECs or HUVSMCs in 100 μL of Dulbecco's Modified Eagle medium (DMEM) with 10% foetal bovine serum (FBS) was seeded onto polyurethane films and glass control (n=3). After incubation for 10 h, 400 μL fresh medium was added and immediately sucked out to remove suspending and loosely adhered cells.

Adhered cells were fixed twice in 400 μL of an ethanol and glacial acetic acid mixture (3:1 (v/v)) for 3 min each. After three washes with water for 2 min each, cells were stained with 400 μL of Hoechst 33258 solution (10 μg/mL, from Sigma, USA) at 37° C. for 15 min, followed by gently rinsing in water three times. Stained cell nuclei were observed under an Olympus DP70 fluorescence microscope (Olympus, Japan).

The morphology of Hoechst stained cells on polyurethanes (FIG. 12) showed that PCUL2-PO-VEGF captured abundant endothelial cells (ECs) while repelled smooth muscle cells (SMCs). PCUL2-PO repelled both cells and glass control adsorbed both cells. The results indicated that VEGF-grafted PCUL2-PO can selectively recruit endothelial cells.

Application Example 4

This example tested the HUVEC growth on the surface of the comb-like functional polyurethane that grafted with VEGF, and verify that grafted VEGF can promote an angiogenic cell growth (e.g. formation of an endothelial vascular tube morphology).

To further test the functions of HUVECs on VEGF-grafted PCUL2-PO, another VEGF grafting prior to cell culture was conducted using 1% (w/v) PCUL2-PO hydrocolloid to prepare test film. One gram of PCUL2-PO was dissolved in 50 mL of DMF and slowly dropped into 200 mL of distilled water under magnetically stirring. The polyurethane macromolecules reorganized to form a core-shell hydrocolloid stabilized by the hydrophilic PEG side chain. The colloid was filtered and dialyzed against 1000 mL of water for 3 d, with 3 water changes per day. The purified hydrocolloid was concentrated to about 100 mL, corresponding to a concentration of 1% (v/w).

One hundred and fifty μL of PCUL2-PO hydrocolloid was added into individual wells of a 96-well plate so that uniform polyurethane films fully covered the well bottoms (0.32 cm$^2$) after water evaporation at 50° C. for 3 days. The films were sterilized by ethylene oxide and conditioned in sterile water at 37° C. for 24 h to equilibrate their surface composition prior to VEGF grafting.

Fifty μL of VEGF 165 solution (diluted with water) at concentrations of 0, 50, 500, 5000, 10000, and 50000 ng/mL were added onto films prepared on the well bottoms of 96-well plate and incubated at 37° C. for 40 h. The bound VEGF amount was obtained by subtracting the supernatant VEGF amount (estimated by ELISA) from the feed VEGF amount. VEGF-grafted samples were labeled by adding the feed VEGF concentration after "PCUL2-PO—" (for example, PCUL2-PO-50 was incubated with 50 ng/mL VEGF).

Three thousand HUVECs in 100 μL DMEM supplemented with 10% FBS was added to each VEGF-grafted film and incubated at 37° C. for 10 h to allow cell adhesion. The medium was refreshed to remove loosely adhered cells. The medium was exchanged every 2 days thereafter. Cell morphology was observed under an Olympus IX 71 inverted microscope (Olympus, Japan) at 1, 3, 5 and 8 days.

Morphological observation revealed cell functionality on VEGF-grafted samples. The cell morphology on PCUL2-PO-0 (i.e., PCUL2-PO without VEGF grafting) is not shown because it was very similar to the cell morphology on PCUL2-PO-50. As shown in FIG. 13A, PCUL2-PO-50 (with $7.33 \pm 0.05$ ng/cm$^2$ VEGF) did not support extended cell adhesion. Most cells formed clusters on it without spreading at day 1 and no spread cells could be found at day 5. The cell density decreased with time. Cells on PCUL2-PO-5000 and -10000 (with $593 \pm 15$ and $1102 \pm 30$ ng/cm$^2$ VEGF) were denser than on PCUL2-PO-50, but with similar morphology (images are not shown). These morphologies were quite different to those on TPS control (FIG. 13B) where cells were well-spread initially and reached confluence in 5 days, showing a cobblestone morphology.

PCUL2-PO-500 (FIG. 13C) with a VEGF density of $72.4 \pm 0.6$ ng/cm$^2$, on the other hand, induced well-spread cells at day 1, followed by cell-cell contact formation after 3 days. Cell loops began to appear by day 5, which indicates the beginning of vascular tubulogenesis on a two dimensional surface. At day 8, the morphology had evolved to form many circular structures surrounded by elongated cells (i.e., vascular tubules). The cell density increased with time. The angiogenic morphologies on this sample showed that cells functioned very well. PCUL2-PO-50000 (with a VEGF density of $4800 \pm 160$ ng/cm$^2$) showed similar morphological change with time (images are not shown). The results indicated that VEGF-grafted PCUL2-PO with an appropriate VEGF density can selectively recruit endothelial cells, support their proliferation and induce strong angiogenic response like vascular tubulogenesis. These VEGF-grafted functional polyurethanes can therefore be used as material candidates for vascular prostheses to promote endothelialization for long-term antithrombogenicity.

The invention claimed is:
1. A method for preparing a polyurethane, the method comprising:
   1) adding 1 part by mole of a diol having a number-average molecular weight of between 500 and 4000 to a reaction vessel, stirring and heating the diol to a temperature of between 100 and 120° C., vacuum dehydrating the diol for between 90 and 240 minutes, and cooling the diol to a temperature of between 50 and

80° C.; adding between 1.58 and 7.10 parts by mole of a diisocyanate to the diol, and pre-polymerizing the diisocyanate and the diol under vacuum at the temperature of between 50 and 80° C. for between 1 and 4 hrs to yield a polyurethane prepolymer;
2) dissolving between 0.5 and 6 parts by mole of lysine in a first solvent to yield a first solution, adding the first solution to the polyurethane prepolymer and stirring for between 10 and 30 min to yield a first reaction mixture; stopping stirring and allowing the first reaction mixture to stand for between 10 and 12 hrs, pouring the first reaction mixture into water, and drying a resulting precipitate at room temperature to yield a polyurethane elastomer containing carboxyl groups;
3) dissolving the polyurethane elastomer containing between 0.5 and 2 parts by mole of the carboxyl groups in a second solvent to yield a second solution; adding dicyclohexylcarbodiimide and N-hydroxysuccinimide which are equimolar and are at least 1.2 times the parts by mole of the carboxyl groups in the polyurethane elastomer, and between 0.5 and 2 parts by mole of an amine-terminated polyethylene glycol in sequence to the second solution, and stirring a resulting mixture for between 20 and 30 hrs at room temperature to yield a reaction solution; and
4) adding 0.1 M hydrochloric acid which is between 1 and 3 wt. % of the second solvent to the reaction solution for reaction for between 3 and 6 hrs; filtering a resulting mixture to remove a precipitate from a first filtrate, and dropping the first filtrate into distilled water under stirring to form a uniformly dispersed colloid; filtering the uniformly dispersed colloid to yield a second filtrate; transferring the second filtrate to a dialysis bag having a molecular weight cutoff of between 8000 and 14000, dialyzing the second filtrate in distilled water, changing the distilled water every 4 to 6 hrs, and taking out the dialysis bag after between 5 and 7 days; vacuum freeze drying a colloid in the dialysis bag to yield a functional polyurethane comprising a side chain of amino-terminated polyethylene glycol;

or 1) adding 1 part by mole of a diol having a number-average molecular weight of between 500 and 4000 to a reaction vessel, stirring and heating the diol to a temperature of between 100 and 120° C., vacuum dehydrating the diol for between 90 and 240 minutes, and cooling the diol to the temperature of between 50 and 80° C.; adding between 1.58 and 7.10 parts by mole of a diisocyanate to the diol, and pre-polymerizing the diisocyanate and the diol under vacuum at the temperature of between 50 and 80° C. for between 1 and 4 hrs to yield a polyurethane prepolymer;
2) dissolving between 0.5 and 6 parts by mole of lysine in a first solvent to yield a first solution, adding the first solution to the polyurethane prepolymer and stirring for between 10 and 30 min to yield a first reaction mixture; stopping stirring and allowing the first reaction mixture to stand for between 10 and 12 hrs, pouring the first reaction mixture into water, and drying a resulting precipitate at room temperature to yield a polyurethane elastomer containing carboxyl groups; and
3) dissolving the polyurethane elastomer containing between 1 and 4 parts by mole of the carboxyl groups in a second solvent to yield a second solution, adding between 1 and 4 parts by mole of an epoxy-terminated polyethylene glycol to the second solution to obtain a second reaction mixture, heating the second mixture to the temperature of between 110 and 130° C. under nitrogen protection, stirring for between 20 and 30 hrs; transferring the second reaction mixture to a dialysis bag having a molecular weight cutoff of between 8000 and 14000, dialyzing the second reaction mixture in distilled water, changing the distilled water every 4 to 6 hrs, and taking out the dialysis bag after between 5 and 7 days; vacuum freeze drying a solution in the dialysis bag to yield a functional polyurethane comprising a side chain of epoxy-terminated polyethylene glycol; wherein a dosage of the first solvent satisfies that a solid content of the first reaction mixture is between 26 and 39 wt. %;

a dosage of the second solvent satisfies that polyurethane elastomer containing the carboxyl groups is between 2 and 10 wt. % of the second solution;

the first solvent is a mixed solvent of water and one selected from the group consisting of tetrahydrofuran, N,N-dimethylformamide, N,N-dimethylacetamide, and dimethyl sulfoxide, and a dosage of water accounts for between 10 and 30 wt. % of the mixed solvent;

the second solvent is selected from N,N-dimethylformamide, N,N-dimethylacetamide, or dimethyl sulfoxide; and the number-average molecular weight of the amine-terminated polyethylene glycol or the epoxy-terminated polyethylene glycol is between 200 and 8000.

2. A method for preparing a polyurethane, the method comprising:
a) adding 1 part by mole of a diol having a number-average molecular weight of between 500 and 4000 to a reaction vessel, stirring and heating the diol to a temperature of between 100 and 120° C., vacuum dehydrating the diol for between 90 and 240 minutes, and cooling the diol to the temperature of between 50 and 80° C.; adding between 2.2 and 7.08 parts by mole of a diisocyanate to the diol, and pre-polymerizing the diisocyanate and the diol under vacuum at the temperature of between 50 and 80° C. for between 1 and 4 hrs to yield a polyurethane prepolymer; and
b) dissolving between 0.15 and 2.10 parts by mole of a diamine chain extender containing a side chain of polyethylene glycol in tetrahydrofuran or in a second solvent, adding a resulting solution to the polyurethane prepolymer while stirring to yield a reaction system; stopping heating, allowing to react for between 10 and 15 min; dissolving between 0.5 and 4.5 part by mole of lysine in water to form a lysine solution, and adding the lysine solution to the reaction system for chain extension for between 10 and 30 min; stopping stirring and allowing a reaction mixture to stand for between 10 and 12 hrs; transferring the reaction mixture to a dialysis bag having a molecular weight cutoff of between 8000 and 14000, dialyzing the reaction mixture in distilled water, changing the distilled water every 4 to 6 hrs, and taking out the dialysis bag after between 5 and 7 days; and vacuum freeze drying a solution in the dialysis bag to yield a functional polyurethane comprising a side chain of carboxyl-terminated polyethylene glycol;

wherein a dosage of tetrahydrofuran or the second solvent satisfies that a total weight of added reactants thereto is between 30 and 50 wt. % of the resulting solution;

the content of water is between 10 and 30 wt. % of the weight of the second solvent;

the second solvent is selected from N,N-dimethylformamide, N,N-dimethylacetamide, or dimethyl sulfoxide; and the diamine chain extender containing the side chain of polyethylene glycol is represented by the following formula:

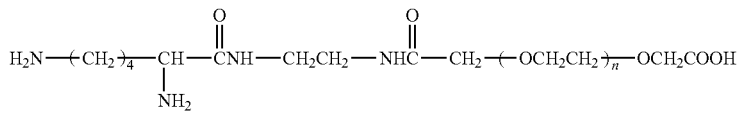

wherein n represents a positive integer ranging from 4 to 180.

3. A polyurethane prepared by the method of claim 1, comprising the side chain of polyethylene glycol having a functional end group; wherein the functional end group is an amino group or an epoxy group; and a peak of the polyethylene glycol appears on a $^1$H-NMR spectrum at a chemical shift of 3.50 ppm and on an infrared spectrum at 1110 cm$^{-1}$.

4. A polyurethane prepared by the method of claim 2, comprising the side chain of polyethylene glycol having a functional end group; wherein the functional end group is a carboxyl group; and a peak of the polyethylene glycol appears on a $^1$H-NMR spectrum at a chemical shift of 3.50 ppm and on an infrared spectrum at 1110 cm$^{-1}$.

5. A method for facilitating growth of endothelial cells in an artificial blood vessel comprising grafting the polyurethane prepared by the method of claim 1 with a vascular endothelial growth factor to selectively recruit vascular endothelial cells and to facilitate angiogenic growth of the vascular endothelial cells; wherein the polyurethane comprises the side chain of polyethylene glycol having an epoxy end group.

* * * * *